US011490660B2

(12) United States Patent
Hawes et al.

(10) Patent No.: US 11,490,660 B2
(45) Date of Patent: Nov. 8, 2022

(54) NICOTINE E-VAPING DEVICE

(71) Applicant: Altria Client Services LLC, Richmond, VA (US)

(72) Inventors: Eric Hawes, Midlothian, VA (US); Raymond W. Lau, Richmond, VA (US); Jose Jesus Paolo Montalvan, Mandaue (PH); John Paul Muring, Lapu-Lapu (PH)

(73) Assignee: Altria Client Services LLC, Richmond, VA (US)

( * ) Notice: Subject to any disclaimer, the term of this patent is extended or adjusted under 35 U.S.C. 154(b) by 282 days.

(21) Appl. No.: 16/911,951

(22) Filed: Jun. 25, 2020

(65) Prior Publication Data
US 2021/0401053 A1    Dec. 30, 2021

(51) Int. Cl.
*A24F 40/485*    (2020.01)
*A24F 40/10*    (2020.01)
*A24F 40/42*    (2020.01)

(52) U.S. Cl.
CPC ............ *A24F 40/485* (2020.01); *A24F 40/10* (2020.01); *A24F 40/42* (2020.01)

(58) Field of Classification Search
CPC ........ A24F 40/485; A24F 40/10; A24F 40/42; A24F 40/40; A61M 2205/8206; A61M 11/042; A61M 15/06
See application file for complete search history.

(56) References Cited

U.S. PATENT DOCUMENTS 9,795,169 B1    10/2017 Zhu
2017/0290370 A1*    10/2017 Garthaffner ............ H05B 3/265
(Continued)

FOREIGN PATENT DOCUMENTS

CA    3122166 A1    6/2020
WO    WO-2016184247    11/2016
(Continued)

OTHER PUBLICATIONS

International Search Report and Written Opinion thereof dated Oct. 29, 2021 for corresponding International Application No. PCT/EP2021/067571.

*Primary Examiner* — Jean F Duverne
(74) *Attorney, Agent, or Firm* — Harness, Dickey & Pierce, P.L.C.

(57) ABSTRACT

A reservoir assembly that holds a nicotine pre-vapor formulation in a reservoir includes a reservoir assembly connector assembly defining a connector conduit, and which may be configured to detachably couple with a nicotine vaporizer assembly based on a connector element of the nicotine vaporizer assembly engaging with the connector conduit of the connector conduit. The reservoir assembly may include an isolation structure configured to move in relation to both the reservoir and the nicotine vaporizer connector assembly between a first position where the isolation structure exposes the nicotine vaporizer assembly to the reservoir and at least partially obstructs the connector conduit to restrict the connector element from disengaging from the connector conduit, and a second position where the isolation structure isolates the nicotine vaporizer assembly from the reservoir and opens the connector conduit to enable the connector element to disengage from the connector conduit.

18 Claims, 17 Drawing Sheets

(56) References Cited

U.S. PATENT DOCUMENTS

| | | | |
|---|---|---|---|
| 2018/0020721 A1* | 1/2018 | Garthaffner | F22B 1/284 |
| | | | 392/404 |
| 2018/0049470 A1 | 2/2018 | Chen | |
| 2018/0228219 A1 | 8/2018 | Qiu | |
| 2018/0255831 A1 | 9/2018 | Lipowicz et al. | |
| 2018/0310614 A1 | 11/2018 | Xu | |

FOREIGN PATENT DOCUMENTS

| WO | WO-2020/002006 A1 | 1/2020 |
|---|---|---|
| WO | WO-2020/084799 A1 | 4/2020 |

\* cited by examiner

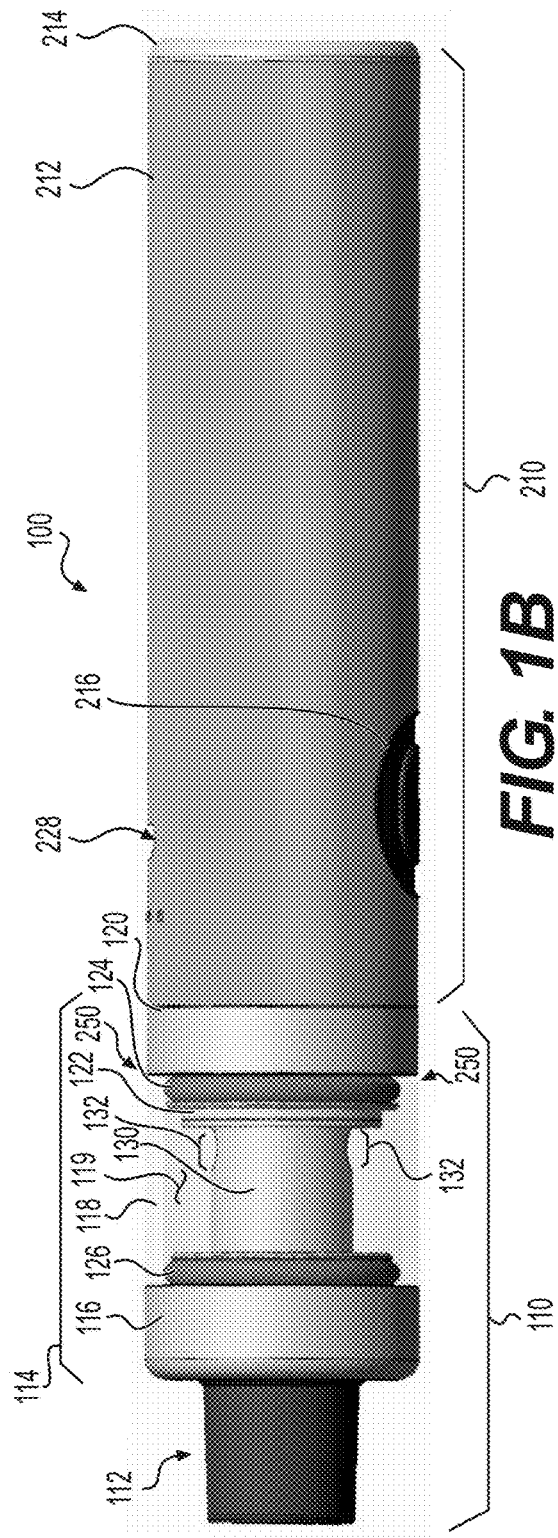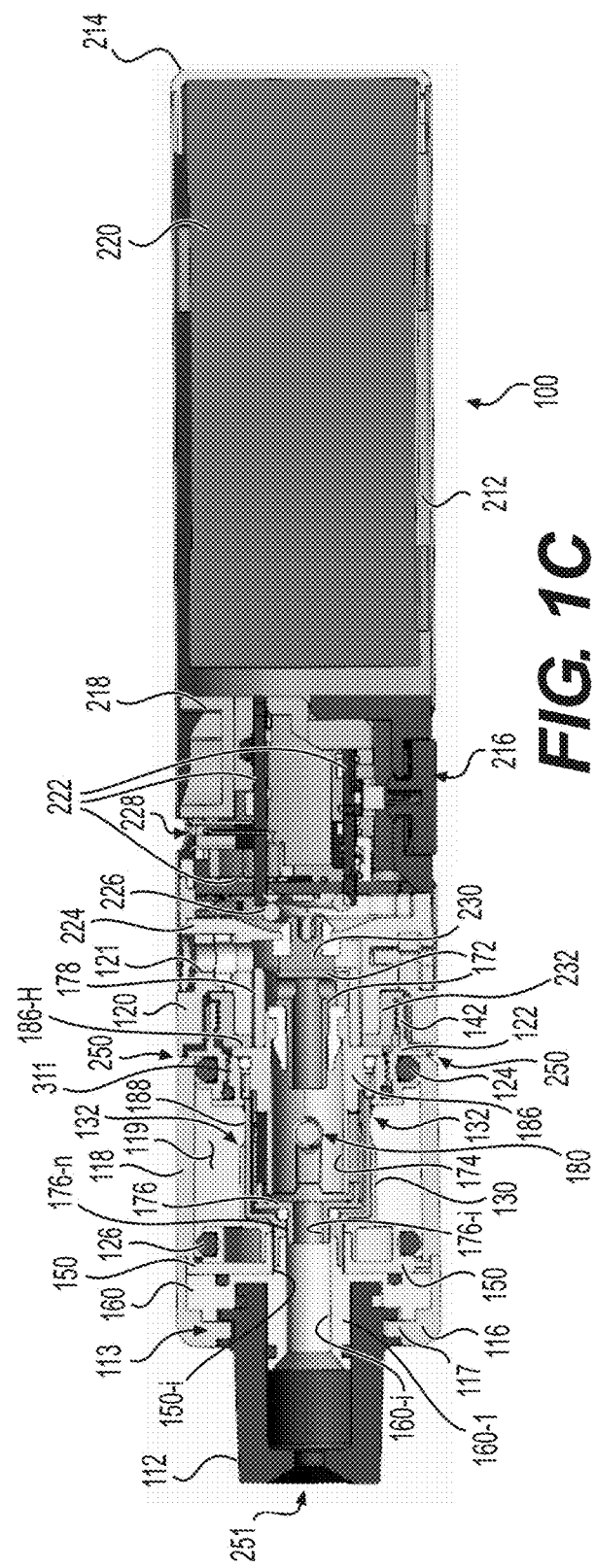

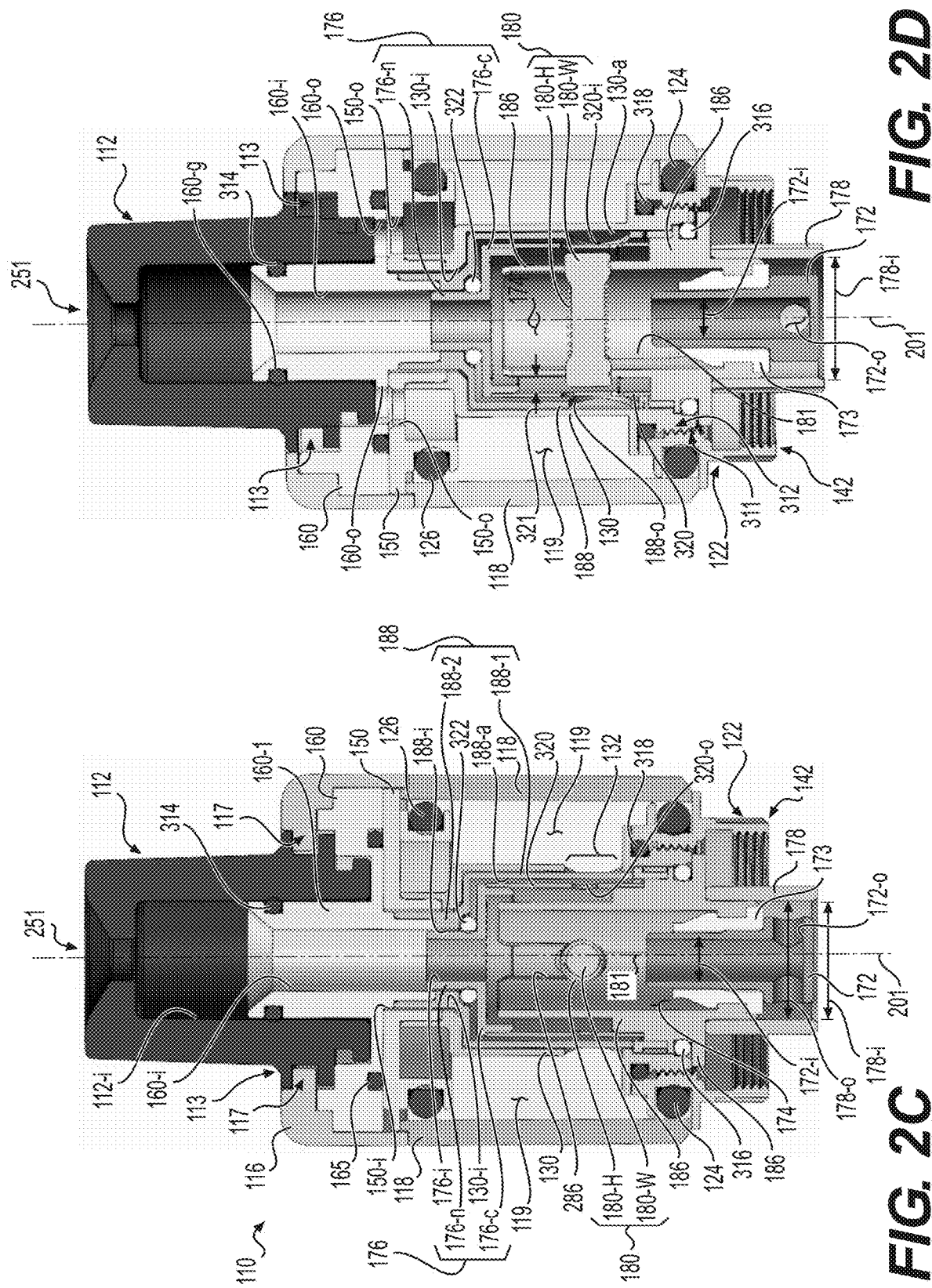

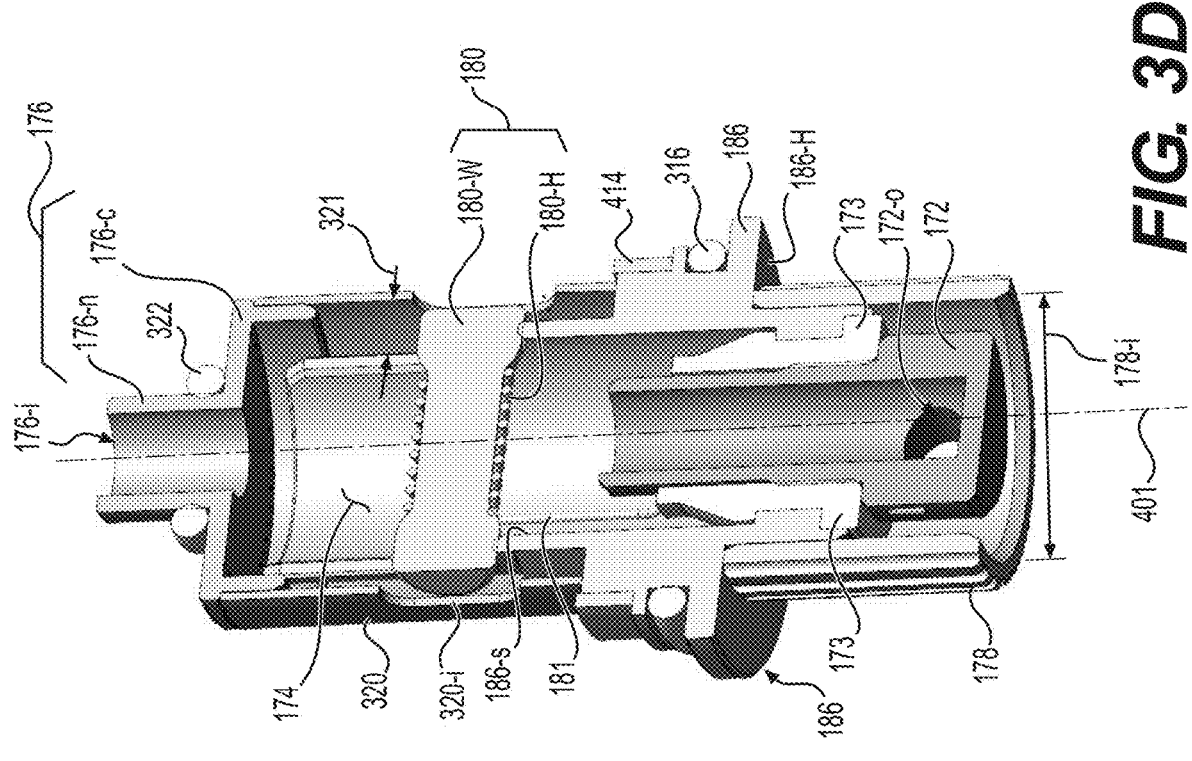
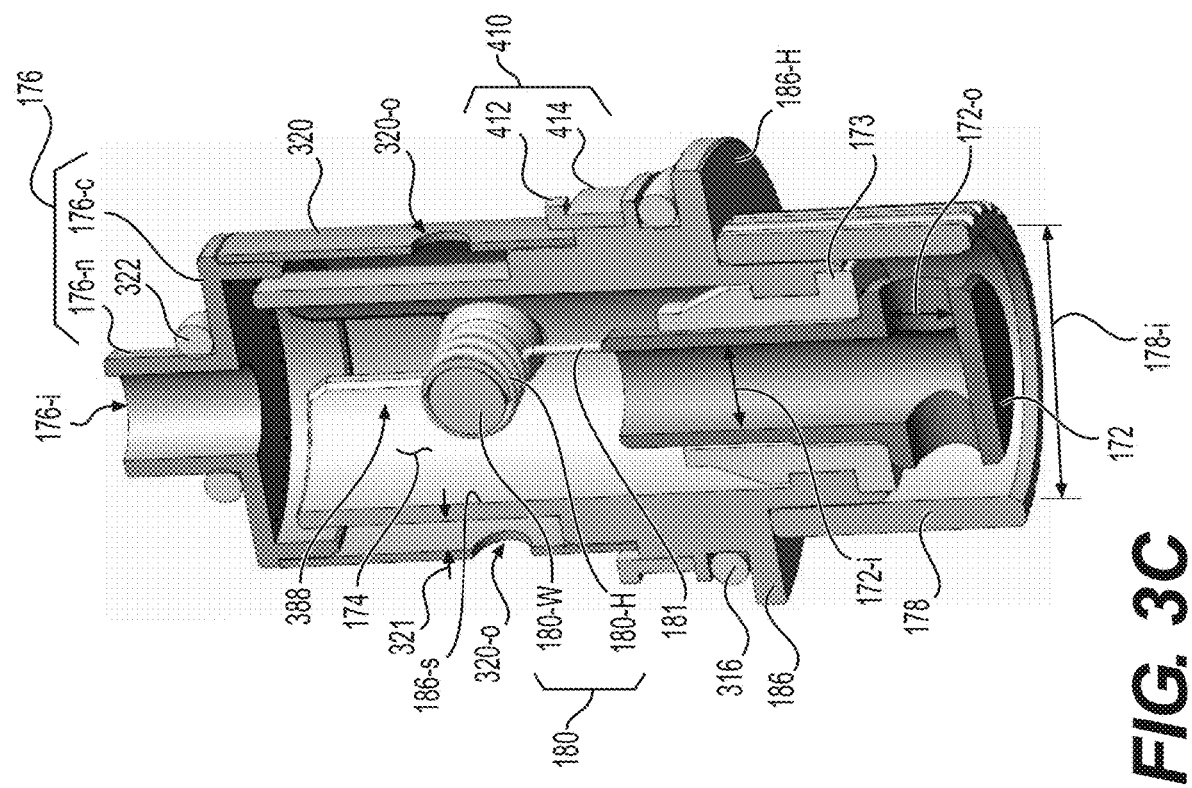
FIG. 3C
FIG. 3D

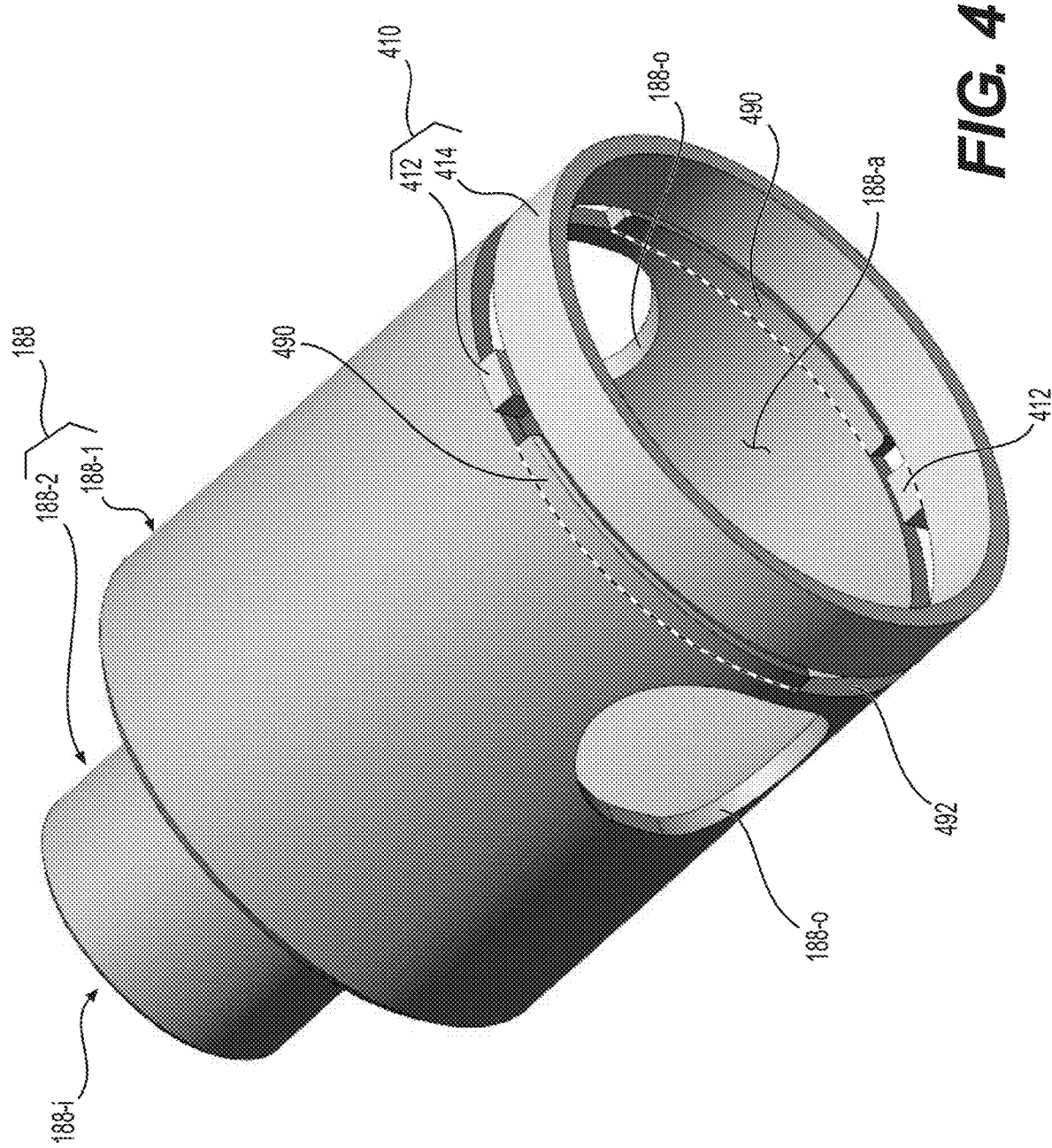

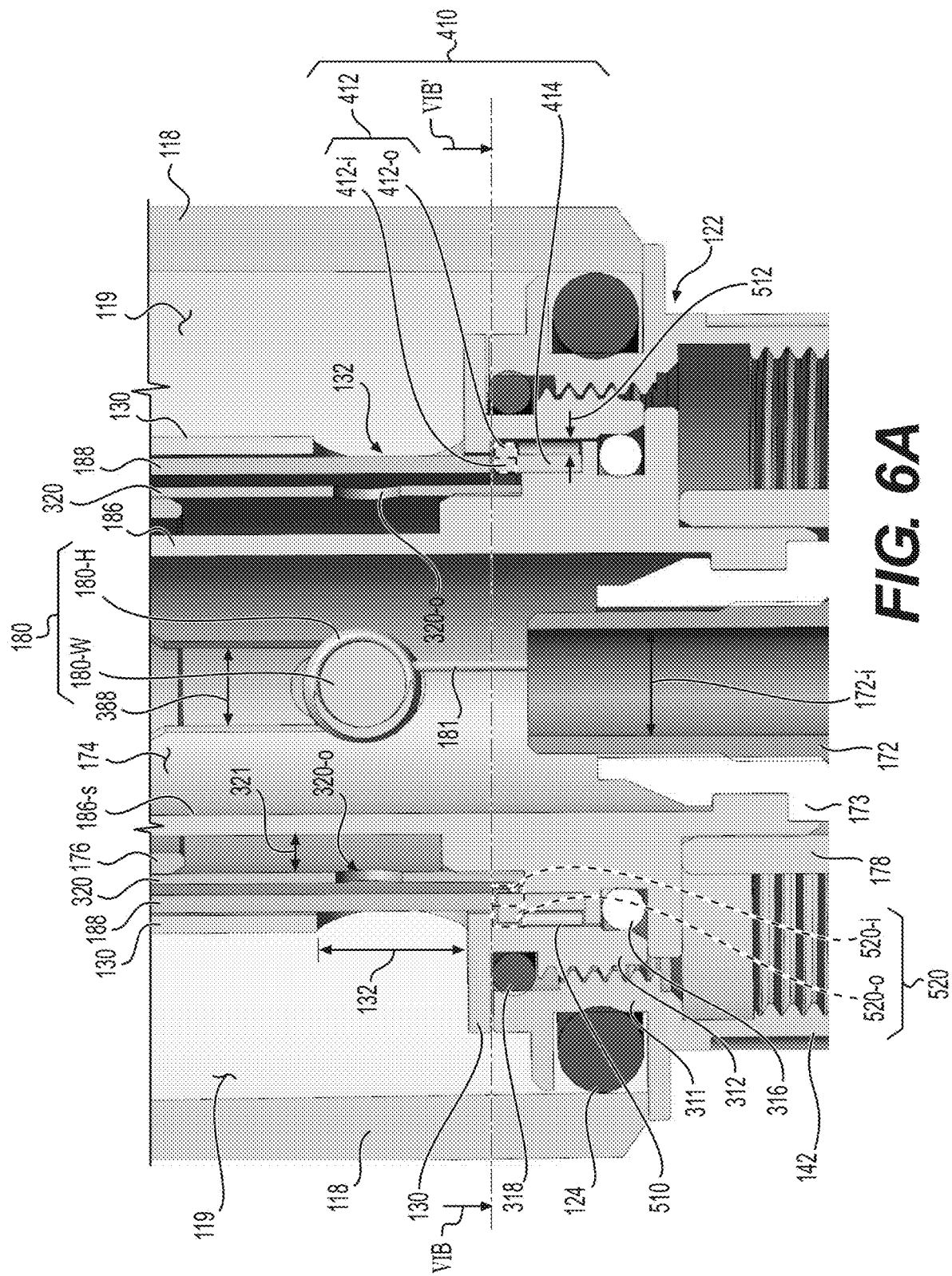

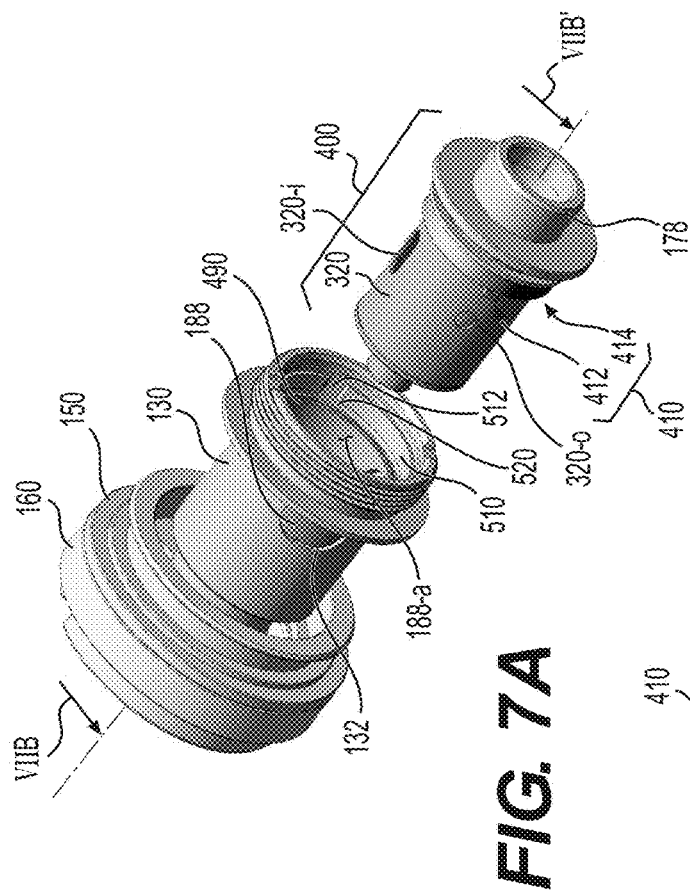
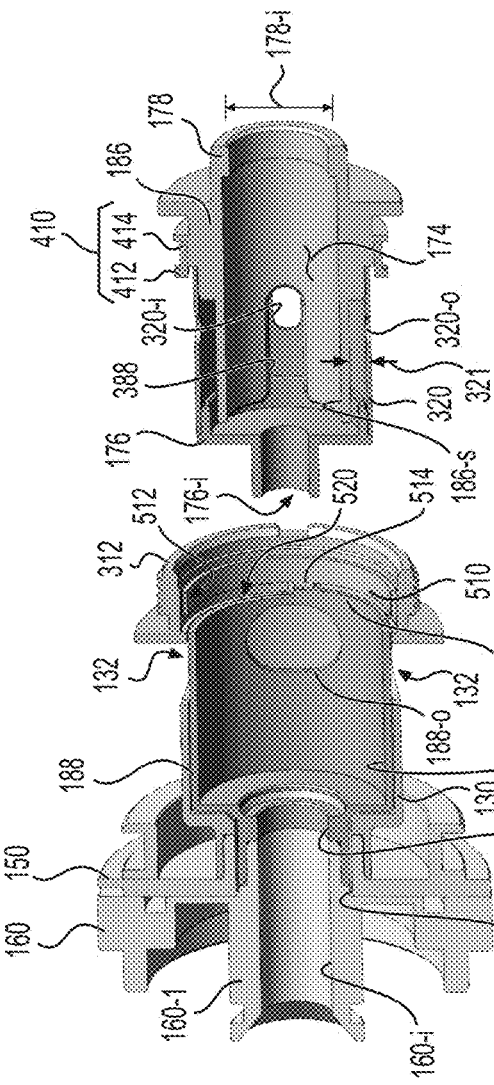
FIG. 7A
FIG. 7B

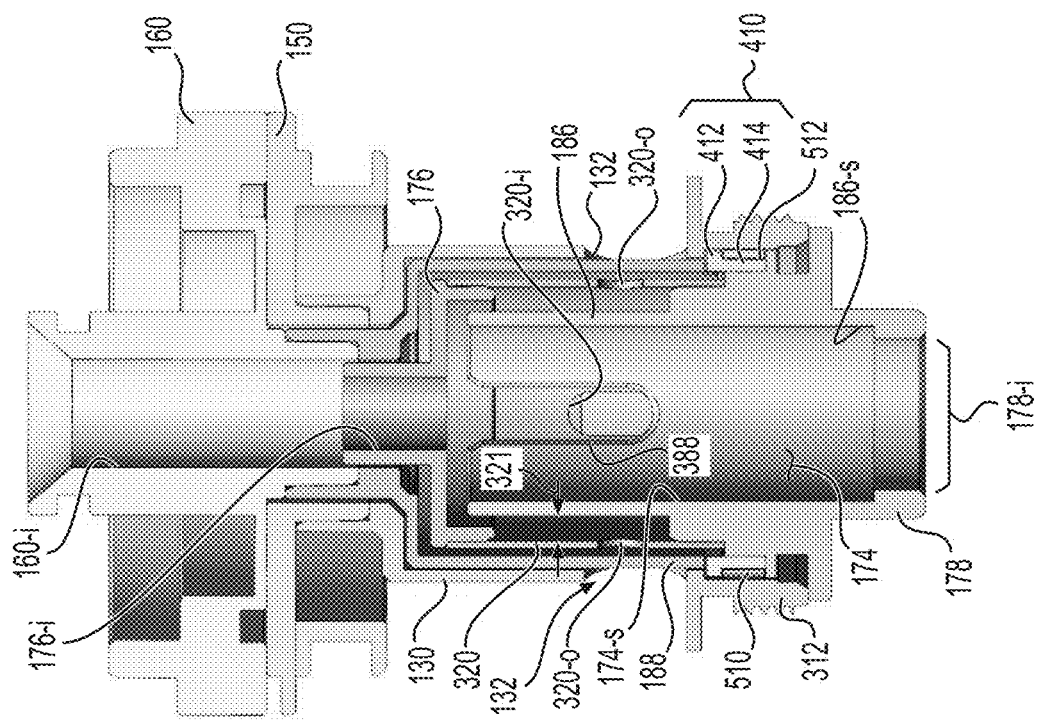
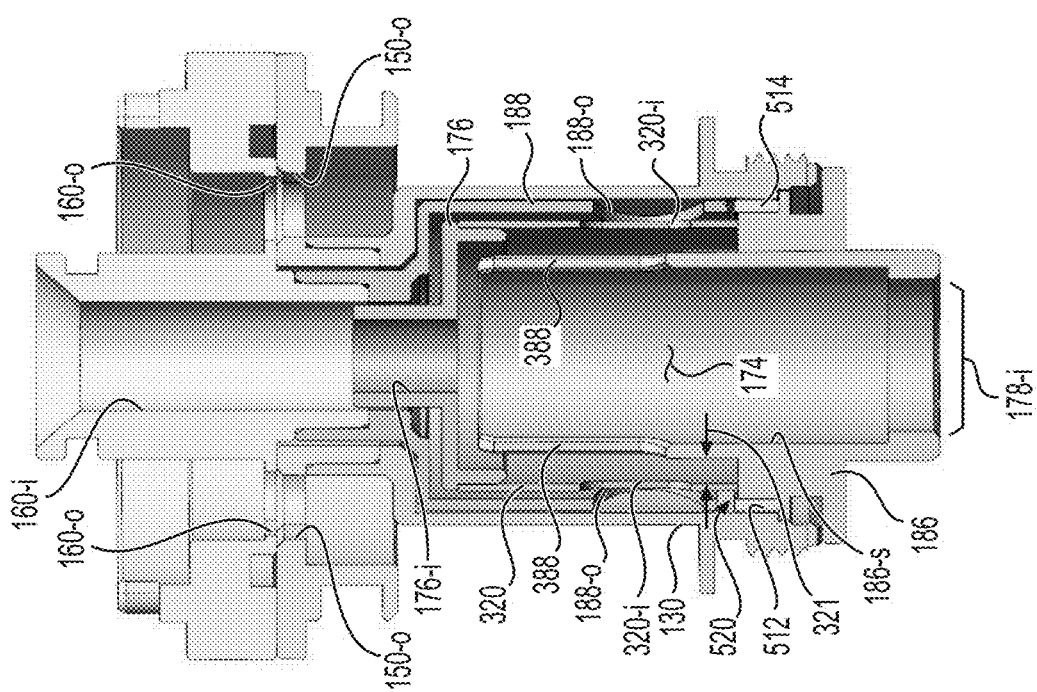

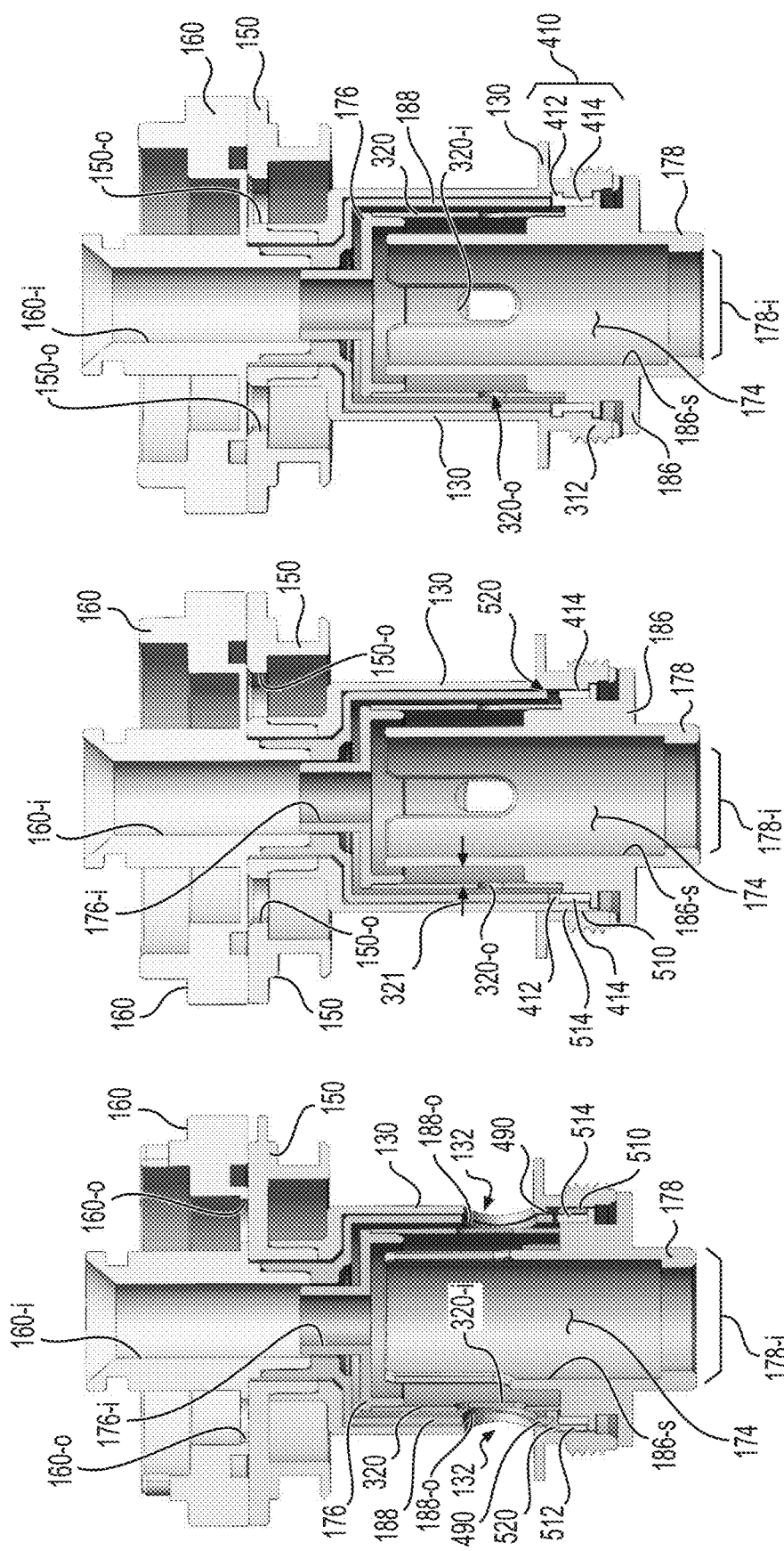

NICOTINE E-VAPING DEVICE

BACKGROUND

Field

Example embodiments relate to nicotine electronic vaping devices, nicotine e-vaping devices, or the like, and/or elements thereof.

Description of Related Art

Nicotine e-vaping devices, also referred to herein as nicotine electronic vaping devices (EVDs) may be used by adult vapers for fluid portable vaping. A nicotine e-vaping device may include a reservoir that holds nicotine pre-vapor formulation and a nicotine vaporizer assembly that may heat nicotine pre-vapor formulation drawn from the reservoir to generate a nicotine vapor.

Some nicotine e-vaping devices are configured to enable replenishment of the nicotine pre-vapor formulation held in a reservoir of the nicotine e-vaping device (i.e., refilling of the reservoir).

SUMMARY

Some example embodiments are directed toward a nicotine e-vaping device.

According to some example embodiments, a nicotine vapor generator assembly may include a reservoir assembly configured to hold a nicotine pre-vapor formulation in a reservoir, and a nicotine vaporizer assembly configured to vaporize the nicotine pre-vapor formulation. The reservoir assembly may further include a reservoir assembly connector assembly defining a connector conduit, the reservoir assembly connector assembly configured to detachably couple with the nicotine vaporizer assembly to establish fluid communication between the nicotine vaporizer assembly and the reservoir based on a connector element of the nicotine vaporizer assembly engaging with the connector conduit. The reservoir assembly may further include an isolation structure configured to move in relation to both the reservoir and the reservoir assembly connector assembly between a first position where the isolation structure exposes the nicotine vaporizer assembly to the reservoir and at least partially obstructs the connector conduit to restrict the connector element from disengaging from the connector conduit, and a second position where the isolation structure isolates the nicotine vaporizer assembly from the reservoir and opens the connector conduit to enable the connector element to disengage from the connector conduit.

The reservoir assembly may include a first fluid port extending through a housing of the reservoir assembly. The isolation structure may be configured to expose the reservoir to the nicotine vaporizer assembly via the first fluid port based on moving to the first position. The isolation structure may be further configured to cover the first fluid port based on moving to the second position.

The reservoir assembly may include a second fluid port, the second fluid port configured to enable fluid communication between the reservoir and an exterior of the nicotine vapor generator assembly. The isolation structure may be configured to cover the second fluid port to isolate the reservoir from the exterior of the nicotine vapor generator assembly based on moving to the first position. The isolation structure may be further configured to expose the second port to expose the reservoir to the exterior of the nicotine vapor generator assembly based on moving to the second position. The reservoir assembly may be configured to be refilled through the second fluid port based on the isolation structure being in the second position.

The isolation structure may be further configured to move in relation to both the reservoir assembly and the reservoir assembly connector assembly to a third position where the isolation structure covers both the first fluid port and the second fluid port. The isolation structure may be configured to open the connector conduit to enable the connector element to disengage from the connector conduit based on the isolation structure moving to the third position.

The isolation structure may include a third fluid port configured to at least partially align with the first fluid port for the isolation structure to expose the first fluid port based on the isolation structure moving to the first position.

The reservoir assembly connector assembly may be a bayonet connector that is configured to establish a bayonet interface connection with a bayonet connector of the nicotine vaporizer assembly.

The isolation structure may be configured to rotate around a longitudinal axis of the reservoir assembly to move between the first position and the second position.

According to some example embodiments, a nicotine e-vaping device may include the nicotine vapor generator assembly and a power supply assembly coupled to the nicotine vapor generator assembly. The power supply assembly may include a power supply. The power supply assembly may be configured to supply electrical power from the power supply to the nicotine vaporizer assembly.

The power supply may be a rechargeable battery.

The power supply assembly may be configured to decouple from the nicotine vapor generator assembly.

According to some example embodiments, a reservoir assembly for a nicotine e-vaping device may include one or more structures defining a reservoir configured to hold a nicotine pre-vapor formulation. The reservoir assembly may include a reservoir assembly connector assembly defining a connector conduit, the reservoir assembly connector assembly configured to detachably couple with a nicotine vaporizer assembly to establish fluid communication between the nicotine vaporizer assembly and the reservoir based on a connector element of the nicotine vaporizer assembly engaging with the connector conduit. The reservoir assembly may include an isolation structure configured to move in relation to both the reservoir and the reservoir assembly connector assembly between a first position where the isolation structure exposes the nicotine vaporizer assembly to the reservoir and at least partially obstructs the connector conduit to restrict the connector element from disengaging from the connector conduit, and a second position where the isolation structure isolates the nicotine vaporizer assembly from the reservoir and opens the connector conduit to enable the connector element to disengage from the connector conduit.

The reservoir assembly may include a first fluid port extending through a housing of the reservoir assembly. The isolation structure may be configured to expose the reservoir to the nicotine vaporizer assembly via the first fluid port based on moving to the first position. The isolation structure may be further configured to cover the first fluid port based on moving to the second position.

The reservoir assembly may include a second fluid port. The second fluid port may be configured to enable fluid communication between the reservoir and an exterior of the reservoir assembly. The isolation structure may be configured to cover the second fluid port to isolate the reservoir from the exterior of the reservoir assembly based on moving to the first position. The isolation structure may be further configured to expose the second fluid port to expose the reservoir to the exterior of the reservoir assembly based on moving to the second position. The reservoir assembly may be configured to be refilled through the second fluid port based on the isolation structure being in the second position.

The isolation structure may be further configured to move in relation to both the reservoir assembly and the reservoir assembly connector assembly to a third position where the isolation structure covers both the first fluid port and the second fluid port. The isolation structure may be configured to open the connector conduit to enable the connector element to disengage from the connector conduit based on the isolation structure moving to the third position.

The isolation structure may include a third fluid port configured to at least partially align with the first fluid port for the isolation structure to expose the first fluid port based on the isolation structure moving to the first position.

The reservoir assembly connector assembly may be a bayonet connector that is configured to establish a bayonet interface connection with a bayonet connector of the nicotine vaporizer assembly.

The isolation structure may be configured to rotate around a longitudinal axis of the reservoir assembly to move between the first position and the second position.

The isolation structure may be configured to move axially along a longitudinal axis of the isolation structure to move between the first position and the second position.

BRIEF DESCRIPTION OF THE DRAWINGS

The various features and advantages of the non-limiting example embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1B is a side view of the nicotine e-vaping device of FIG. 1A according to some example embodiments.

FIG. 1C is a cross-sectional view along line IC-IC' of the nicotine e-vaping device of FIGS. 1A-1B according to some example embodiments.

FIG. 2C is a cross-sectional view along line IIC-IIC' of the nicotine vapor generator assembly of FIGS. 2A-2B according to some example embodiments.

FIG. 2D is a cross-sectional view along line IID-IID' of the nicotine vapor generator assembly of FIGS. 2A-2B according to some example embodiments.

FIG. 3C is a cross-sectional perspective view along line IIIC-IIIC' of the nicotine vaporizer assembly of FIGS. 3A-3B according to some example embodiments.

FIG. 3D is a cross-sectional perspective view along line IIID-IIID' of the nicotine vaporizer assembly of FIGS. 3A-3B according to some example embodiments.

FIG. 4 is a perspective view of an isolation structure according to some example embodiments.

FIG. 6A is a cross-sectional view of the nicotine vapor generator assembly of FIGS. 2A-2B according to some example embodiments.

FIG. 7A is a perspective view of a reservoir assembly and a nicotine vaporizer assembly aligned with the longitudinal axis of the reservoir assembly according to some example embodiments.

FIG. 7B is a cross-sectional view of the reservoir assembly and aligned nicotine vaporizer assembly of FIG. 7A along view line VIIB-VIIB'.

FIG. 8C is a cross-sectional view along line VIIIC-VIIIC' of the reservoir assembly and nicotine vaporizer assembly of FIG. 8A according to some example embodiments.

FIG. 8D is a cross-sectional view along line VIIID-VIIID' of the reservoir assembly and nicotine vaporizer assembly of FIG. 8A according to some example embodiments.

FIG. 9C is a cross-sectional view along line IXC-IXC' of the reservoir assembly and nicotine vaporizer assembly of FIG. 9A according to some example embodiments.

FIG. 9D is a cross-sectional view along line IXD-IXD' of the reservoir assembly and nicotine vaporizer assembly of FIG. 9A according to some example embodiments.

FIG. 9E is a cross-sectional view along line IXE-IXE' of the reservoir assembly and nicotine vaporizer assembly of FIG. 9A according to some example embodiments.

DETAILED DESCRIPTION OF EXAMPLE EMBODIMENTS

Figure 1A:
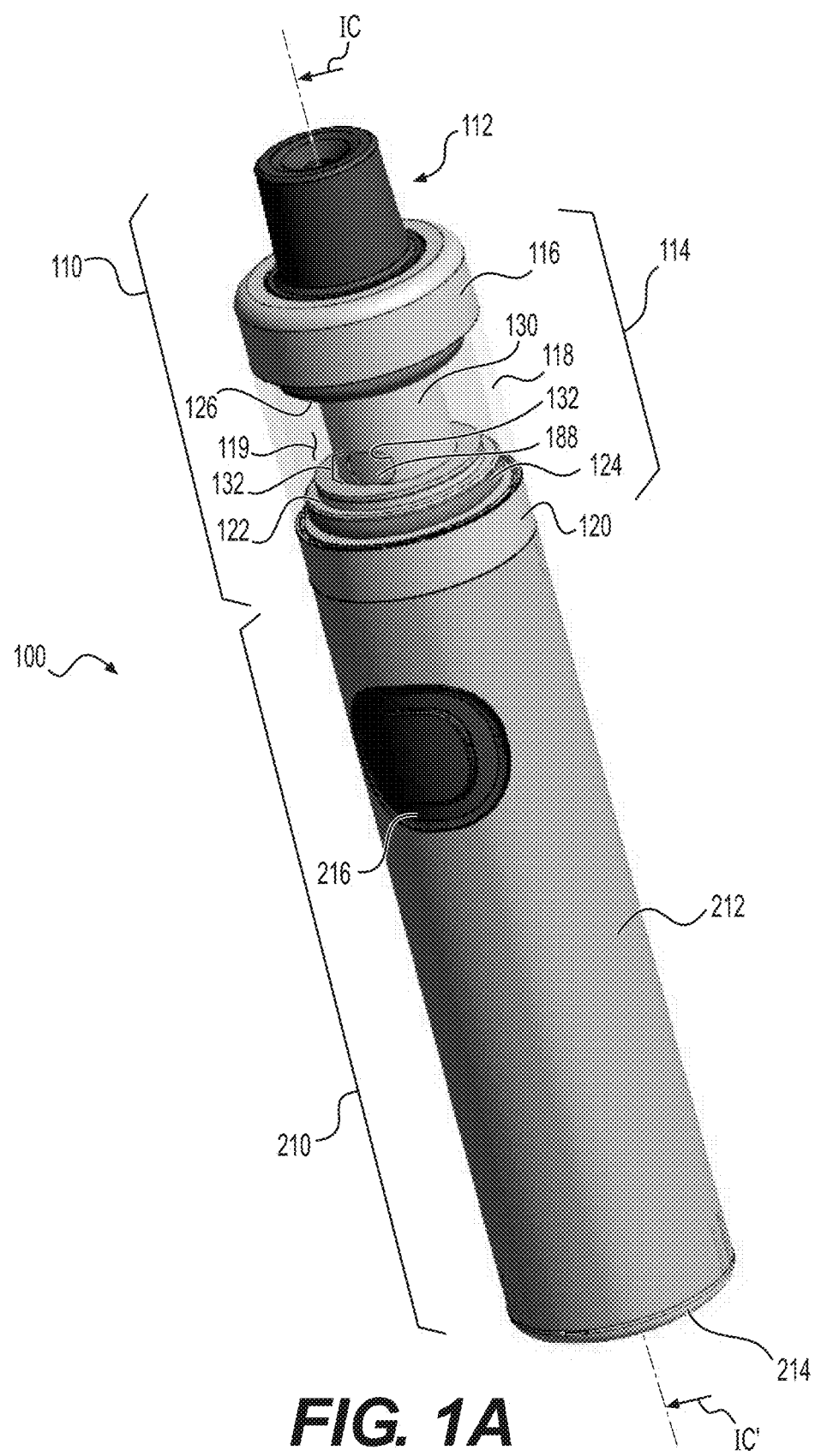
FIG. 1A is a perspective view of a nicotine e-vaping device according to some example embodiments.

Some detailed example embodiments are disclosed herein. However, specific structural and functional details disclosed herein are merely provided for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element, or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, etc., but do not preclude the presence or addition of one or more other features, integers, steps, operations, elements, etc., and/or groups thereof.

When the words "about" and "substantially" are used in this specification in connection with a numerical value, it is intended that the associated numerical value include a tolerance of ±10% around the stated numerical value, unless otherwise explicitly defined.

Example embodiments are described herein with reference to cross-sectional illustrations that are schematic illustrations of example embodiments. As such, variations from the shapes of the illustrations are to be expected. Thus, example embodiments should not be construed as limited to the shapes of regions illustrated herein but are to include deviations in shapes.

Nicotine vapor, nicotine aerosol and nicotine dispersion are used interchangeably and are meant to cover the matter generated or outputted by the devices disclosed, claimed and/or equivalents thereof wherein such matter contains nicotine. The nicotine e-vaping devices as described herein may each be regarded as an electronic nicotine delivery system (ENDS).

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 2B:
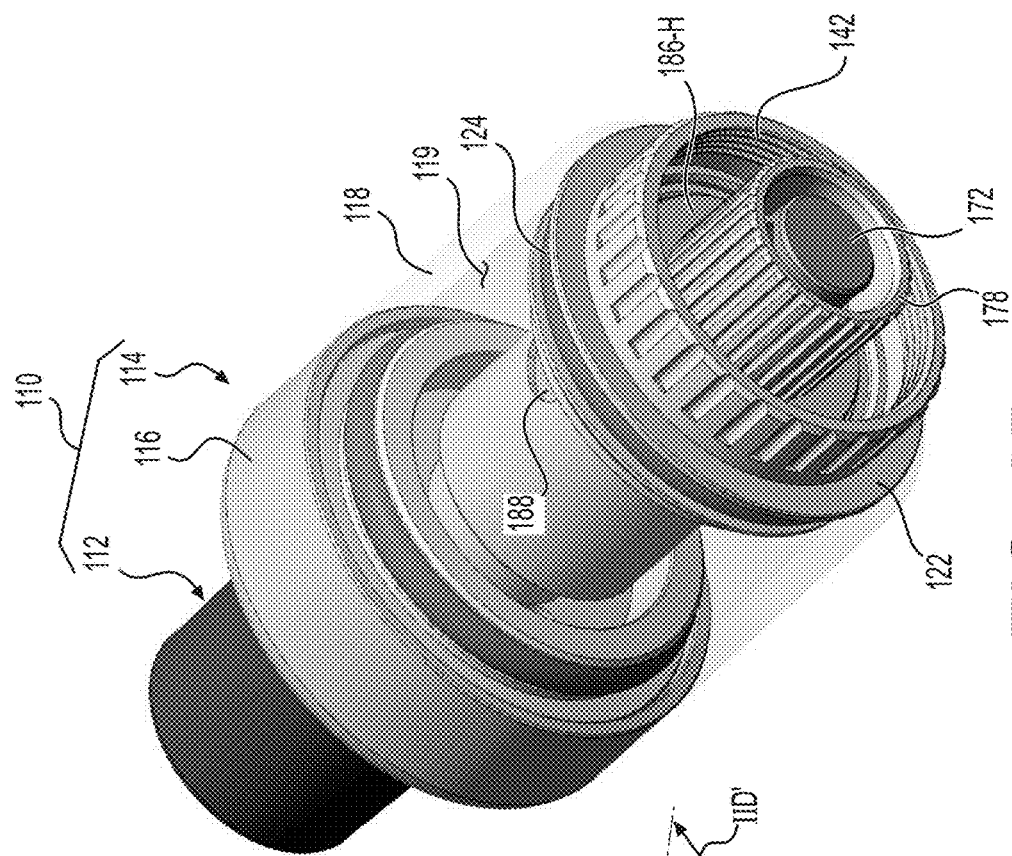
FIGS. 2A-2B are perspective views of a nicotine vapor generator assembly according to some example embodiments.
Figure 2A:
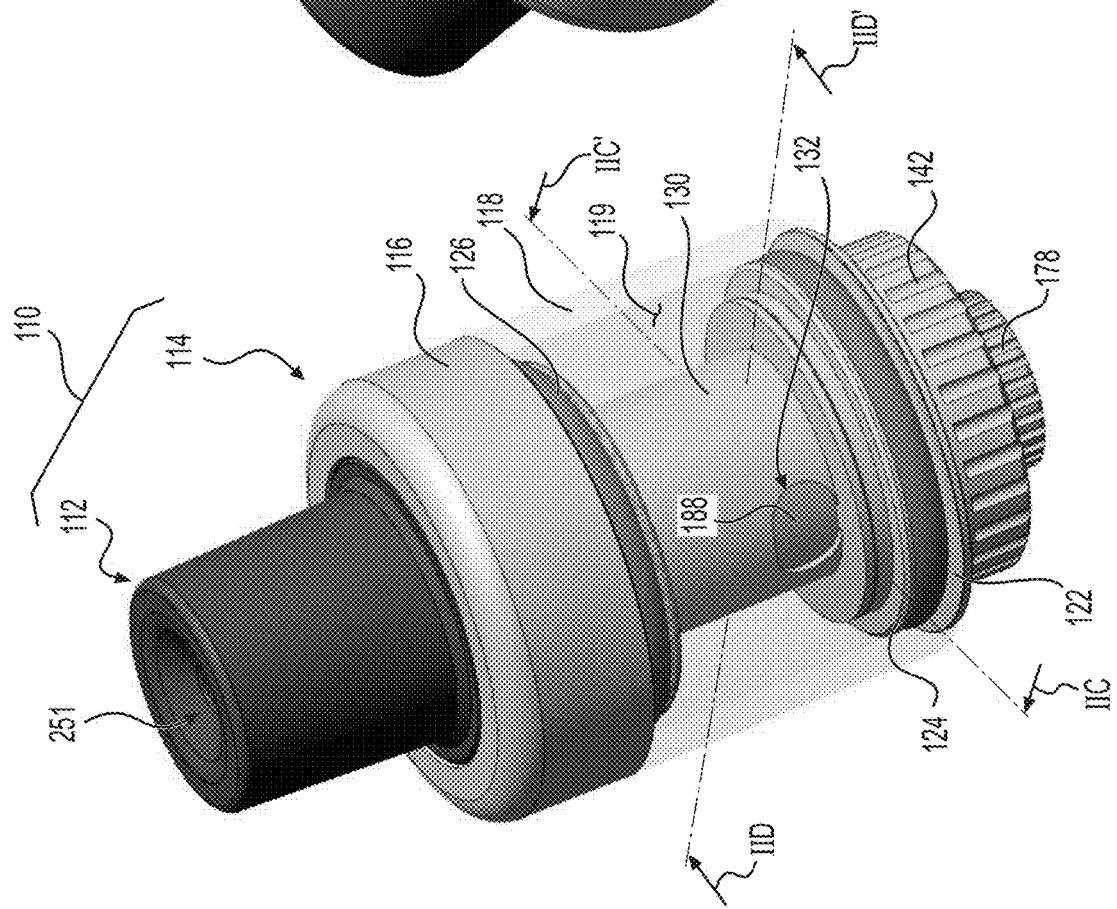

FIG. 1A is a perspective view of a nicotine e-vaping device according to some example embodiments. FIG. 1B is a side view of the nicotine e-vaping device of FIG. 1A according to some example embodiments. FIG. 1C is a cross-sectional view along line IC-IC' of the nicotine e-vaping device of FIGS. 1A-1B according to some example embodiments. As used herein, the term "nicotine e-vaping device" is inclusive of all types of nicotine electronic vaping devices, regardless of form, size or shape. FIGS. 2A-2B are perspective views of a nicotine vapor generator assembly 110 according to some example embodiments. FIG. 2C is a cross-sectional view along line IIC-IIC' of the nicotine vapor generator assembly 110 of FIGS. 2A-2B according to some example embodiments. FIG. 2D is a cross-sectional view along line IID-IID' of the nicotine vapor generator assembly 110 of FIGS. 2A-2B according to some example embodiments.

Referring to FIGS. 1A-1C, the nicotine e-vaping device 100 includes a nicotine vapor generator assembly 110 and a power supply assembly 210. In some example embodiments, the nicotine vapor generator assembly 110 and power supply assembly 210 include respective complementary connector assemblies 142, 232 and are configured to be detachably connected to each other based on detachably coupling the connector assemblies 142, 232 together. In some example embodiments, a nicotine vapor generator assembly 110 that is configured to be detachably coupled to a power supply assembly 210 to form a nicotine e-vaping device 100 may be referred to herein as a cartridge. In some example embodiments, the connector assemblies 142 include threaded connectors. It should be appreciated that a connector assembly 142, 232 may be any type of connector, including, without limitation, a snug-fit, detent, clamp, bayonet, sliding fit, sleeve fit, alignment fit, threaded connector, magnetic, clasp, or any other type of connection, and/or combinations thereof. In some example embodiments, the nicotine e-vaping device 100 may be a unitary piece that includes the nicotine vapor generator assembly 110 and the power supply assembly 210 in the unitary piece, instead of including the nicotine vapor generator assembly 110 and the power supply assembly 210 as separate pieces that are coupled together to form the nicotine e-vaping device 100.

As shown in at least FIGS. 2A-2D, the nicotine vapor generator assembly 110 may include at least a reservoir 119 that is configured to hold a nicotine pre-vapor formulation, a nicotine vaporizer assembly 400 that is configured to heat nicotine pre-vapor formulation drawn from the reservoir 119 to generate a nicotine vapor, and an isolation structure 188 configured to adjustably expose or isolate the nicotine vaporizer assembly 400 in relation to the reservoir 119. As further shown, the nicotine vapor generator assembly 110 may include an outlet assembly 112, but it will be understood that in some example embodiments the outlet assembly 112 may be omitted. As shown in FIGS. 1A-1C, the reservoir 119 and the isolation structure 188 may be included in a reservoir assembly 114 of some example embodiments, where the reservoir assembly 114 and the nicotine vaporizer assembly 400 may be coupled together to at least partially establish the nicotine vapor generator assembly 110. The isolation structure 188 and its connections with elements of the reservoir assembly 114 are illustrated in further detail in FIGS. 4 and 5A-5C.

A nicotine pre-vapor formulation is a material or combination of materials that may be transformed into a nicotine vapor. For example, the nicotine pre-vapor formulation may include a liquid, solid, and/or gel formulation. These may include, for example and without limitation, water, oil, emulsions, beads, solvents, active ingredients, ethanol, plant extracts, nicotine, natural or artificial flavors, vapor formers such as glycerin and propylene glycol, and/or any other ingredients that may be suitable for vaping.

As shown in at least FIGS. 1A-1C, 2C-2D, and 5A-5B, the reservoir assembly 114 may include an upper structure 150, a lower structure 122, an outer housing 118, and an inner housing 130 that may collectively at least partially define the reservoir 119 as an annular space bounded by respective surfaces of at least the upper structure 150, lower structure 122, outer housing 118, and inner housing 130. As shown, the reservoir assembly 114 may be configured to hold a nicotine pre-vapor formulation within the reservoir 119.

As shown in at least FIGS. 2A-2D, a ring gasket 126 may establish a seal of the interface of the upper structure 150 and an inner surface of the outer housing 118, and a ring gasket 124 may establish a seal of the interface of the lower structure 122 and an inner surface of the outer housing 118, to mitigate leakage of nicotine pre-vapor formulation from the reservoir 119 to an exterior of the reservoir assembly 114 via the aforementioned interfaces. The inner housing 130 may be coupled to the lower structure 122 via respective, complementary connectors 312, 311, and a ring gasket 318 may establish a seal of the interface of the inner housing 130 and the lower structure 122 to mitigate leakage of nicotine pre-vapor formulation from the reservoir 119 to an exterior of the reservoir assembly 114 via the aforementioned interface. As shown, the connectors 311, 312 may include threaded connectors, but it should be appreciated that a connector 311, 312 may be any type of connector, including, without limitation, a snug-fit, detent, clamp, bayonet, sliding fit, sleeve fit, alignment fit, threaded connector, magnetic, clasp, or any other type of connection, and/or combinations thereof.

As shown in at least FIG. 2D, the upper structure 150 may include one or more fluid ports 150-o, also referred to as one or more second fluid ports, which extend through the upper structure 150 between the reservoir 119 and an exterior of at least the reservoir 119, such that the one or more fluid ports 150-o may enable fluid communication between the reservoir 119 and the exterior of at least the reservoir 119. As shown in at least FIGS. 1C and 2C-2D, the reservoir assembly 114 may include a coupling structure 160 that is configured to be adjacent to the upper structure 150 and is configured to rotate, around a longitudinal axis 201 of the reservoir assembly 114, in relation to the upper structure 150. A ring gasket 165 may seal an interface between the upper structure 150 and the coupling structure 160, to mitigate leakage of nicotine pre-vapor formulation from the reservoir 119 via the aforementioned interface. The coupling structure 160 may include one or more fluid ports 160-o which extend through the coupling structure 160. As shown in at least FIG. 2D, in some example embodiments, each fluid port 150-o may be aligned with a separate fluid port 160-o, in a direction extending coaxially with the longitudinal axis 201, such that reservoir assembly 114 is configured to enable fluid communication between the reservoir 119 and the exterior of the reservoir assembly 114 via the longitudinally-aligned fluid ports 150-o, 160-o. In some example embodiments, the coupling structure 160 is configured to rotate, in relation to the upper structure 150, around the longitudinal axis 201 to adjustably longitudinally align or mis-align the one or more fluid ports 160-o with the one or more fluid ports 150-o and thereby to adjustably expose or isolate the reservoir 119 to an exterior of the reservoir assembly 114, to enable re-filling of the reservoir 119 with nicotine pre-vapor formulation when the reservoir 119 is exposed to the exterior of the reservoir assembly 114.

Still referring to at least FIGS. 1C and 2C-2D, the reservoir assembly 114 may include a port adjustment ring 116 that is connected to the coupling structure 160 and is configured to cause the coupling structure 160 to rotate around the longitudinal axis 201 based on the port adjustment ring 116 being caused to rotate around the longitudinal axis 201. For example, the port adjustment ring 116 may be fixed to the coupling structure 160 via an adhesive, a weld, a bolt connection, a threaded connection, a bayonet connection, or the like. Accordingly, the reservoir assembly 114 may be configured to enable manually-implemented rotation of the coupling structure 160 in relation to the upper structure 150 to adjustably expose or isolate the reservoir 119 to an exterior of the reservoir assembly 114 via longitudinally-aligned or mis-aligned ports 160-o, 150-o.

Still referring to at least FIGS. 1C and 2C-2D, the nicotine vapor generator assembly 110 may include an outlet assembly 112 that is configured to detachably engage with the coupling structure 160 to reversibly expose or isolate the one or more ports 160-o from an exterior of the nicotine vapor generator assembly 110 and further to establish fluid communication between a conduit extending from the nicotine vaporizer assembly 400 to an exterior of the nicotine vapor generator assembly 110 (described further below) via outlet 251. As shown, the outlet assembly 112 includes an inner conduit 112-i that is configured to receive a nose section of the coupling structure 160. The outlet assembly 112 further includes a projection structure 314, protruding from an inner surface of the inner conduit 112-i, that is configured to be received into a groove structure 160-g of the coupling structure 160 to seal the interface between the conduit 112-i and the nose section 160-1 of the coupling structure 160 to mitigate leakage of fluids passing through the inner conduit 112-*i* from exiting the outlet assembly 112 through passages other than the outlet 251. As shown in FIGS. 2C-2D, the outlet assembly 112 is configured to establish a bayonet connection with the port adjustment ring 116. The port adjustment ring 116 includes a plug bayonet connector 117 and the outlet assembly 112 includes a channel bayonet connector 113 that is complementary to the plug bayonet connector 117. As a result, the outlet assembly 112 is configured to engage the channel bayonet connector 113 with the plug bayonet connector 117 to establish a detachable bayonet connection between the outlet assembly 112 and the coupling structure 160 and thereby to establish a detachable bayonet connection between the reservoir assembly 114 and the outlet assembly 112.

Still referring to at least FIG. 1C and FIGS. 2A-2D, the outlet assembly 112 is configured to cover the one or more ports 160-*o* of the coupling structure 160 based on the outlet assembly 112 establishing the detachable bayonet connection between the outlet assembly 112 and the coupling structure 160, such that the outlet assembly 112 isolates the one or more ports 160-*o* from the exterior of the nicotine vapor generator assembly 110 and thus mitigates leakage of nicotine pre-vapor formulation from the reservoir 119 via ports 150-*o*, 160-*o* when the outlet assembly 112 is coupled to the reservoir assembly 114 via the bayonet connection between the outlet assembly 112 and the coupling structure 160. In addition, the nicotine vapor generator assembly 110 may be configured to enable exposure of the reservoir 119 to an exterior of the nicotine vapor generator assembly 110 based on both the outlet assembly 112 being detached from the coupling structure 160 and the coupling structure 160 further being rotated around the longitudinal axis 201 to longitudinally align the one or more ports 160-*o* of the coupling structure 160 with one or more ports 150-*o* of the upper structure 150.

As shown in at least FIGS. 1C and 2C-2D, the inner housing 130 is connected to the upper structure 150 and is fixed in place in relation to the upper structure 150 (e.g., via an adhesive, a connector, or the like). As shown, the inner surface of the inner housing 130 at least partially defines a barrel conduit 130-*a* and a nose conduit 130-*i* that are configured to receive at least a portion of the nicotine vaporizer assembly 400 to enable the nicotine vaporizer assembly 400 to be coupled with the reservoir assembly 114 to at least partially establish the nicotine vapor generator assembly 110.

As shown in FIGS. 2C-2D and 5A-5B, the inner housing 130 defines a lower-barrel conduit 130-*a* and an upper, nose conduit 130-*i*, where the conduit 130-*i* has a diameter that is at least as great as an outer diameter of a nose segment 176-*n* of the nicotine vaporizer assembly 400 and where the barrel conduit 130-*a* has a diameter that is at least as great as an outer diameter of an outer housing 320 of the nicotine vaporizer assembly 400.

Still referring to at least FIGS. 2C-2D, the upper structure 150 includes a conduit 150-*i* that is configured to be aligned with the nose conduit 130-*i* around the longitudinal axis 201 and to have an inner surface that is flush or substantially flush with an inner surface of the inner housing 130 so that conduits 130-*i* and 150-*i* collectively define a single, continuous conduit.

As shown in FIGS. 1A-2D and FIG. 4 and FIGS. 5A-5C, the reservoir assembly 114 includes an isolation structure 188 that is connected to the coupling structure 160 and is fixed in place in relation to the coupling structure 160 (e.g., via adhesive, welds, connectors, or the like), such that the coupling structure 160 is configured to cause the isolation structure 188 to rotate around the longitudinal axis 201 with the coupling structure 160. As shown in at least FIGS. 2C-2D and 4-5B, the isolation structure 188 includes a barrel structure 188-1 with an inner surface that defines a barrel conduit 188-*o* and a nose structure 188-2 with an inner surface that defines a narrower nose conduit 188-*i*. As shown in FIGS. 2C-2D and 4-5B, the nose structure 188-2 is fixed to the coupling structure 160 such that the nose conduit 188-*i* is directly adjacent to the conduit 160-*i* and at least a portion of the nose structure 188-2 and the coupling structure 160 occupy the conduit defined by conduits 130-*i* and 150-*i* and the barrel structure 188-1 occupies conduit 130-*i*. In some example embodiments, the outer diameters of the barrel structure 188-1 and the nose structure 188-2 may correspond to the inner diameters of the conduits 130-*a* and 130-*i*, respectively, such that an interposing space may be absent or substantially absent between the outer surfaces of the isolation structure 188 and the inner surfaces of the inner housing 130, but example embodiments are not limited thereto.

As shown, in at least FIGS. 2C-2D, the nose structure 188-2 defines a conduit 188-*i* and the barrel structure 188-1 defines a conduit 188-*a* that is wider than conduit 188-*i*. In addition, the coupling structure 160 includes a conduit 160-*i* that is configured to be aligned with the conduit 188-*i* around the longitudinal axis 201 and to have an inner surface that is flush or substantially flush with an inner surface of the nose structure 188-2 so that conduits 188-*i* and 160-*i* collectively define a single, continuous conduit.

As shown, the conduits 188-*i* and 160-*i* are configured to collectively define a conduit that establishes fluid communication between conduit 188-*a* and an exterior of the reservoir assembly 114, independently of reservoir 119. As further shown in FIGS. 2C-2D, the outlet assembly 112 is configured to be detachably connected to the coupling structure 160 such that a nose portion of the coupling structure 160, through which conduit 160-*i* extends, is inserted into the inner conduit 112-*i* of the outlet assembly, such that the outlet 251, inner conduit 112-*i*, and conduit 160-*i* and 188-*i* collectively define a conduit that establishes fluid communication between conduit 188-*a* and an exterior of the nicotine vapor generator assembly 110, independently of reservoir 119.

Still referring to FIGS. 2C-2D and FIGS. 5A-5B, the inner housing 130 includes one or more ports 132, also referred to herein as one or more first fluid ports that extend through the inner housing 130 between the reservoir 119 and the conduit 130-*a* to establish fluid communication therebetween. As further shown, the isolation structure 188 may include one or more ports 188-*o*, also referred to herein as one or more third fluid ports, that extend through the barrel structure 188-1 to establish fluid communication between barrel conduit 188-*a* and an exterior of the isolation structure 188. Based on being fixed to the coupling structure 160, which is configured to be rotated around longitudinal axis 201, the isolation structure 188 may be configured to rotate around the longitudinal axis 201 to adjustably radially align or mis-align the one or more ports 188-*o* with the one or more ports 132 of the inner housing 130, to adjustably expose the barrel conduit 188-*a* with the reservoir 119 or isolate the barrel conduit 188-*a* from the reservoir 119 based on the isolation structure 188 being rotated around longitudinal axis 201.

Referring now to FIGS. 1A-1C, the power supply assembly 210 of the nicotine e-vaping device 100 is now described. Referring to FIG. 1C, an example power supply assembly 210 may include an outer housing 212 and end cap 214 at least partially defining an enclosure. As shown, a power supply 220 may be included within the enclosure of the power supply assembly 210. The power supply 220 may be a rechargeable battery, and the power supply assembly 210 may be configured to supply electrical power from the power supply 220 to the nicotine vapor generator assembly 110 (e.g., to the nicotine vaporizer assembly 400 via one or more electrical leads) to support nicotine vapor generation at the nicotine vaporizer assembly 400.

As shown in FIG. 1C, an example nicotine e-vaping device 100 may include one or more instances of control circuitry 222 that may be configured to control the supply of electrical power from the power supply 220 to the nicotine vapor generator assembly 110 (e.g., to the nicotine vaporizer assembly 400). In the example embodiments shown in FIG. 1B, the control circuitry 222 is included in the power supply assembly 210 and is structurally supported therein by one or more instances of support structure 218. It will be understood that, in some example embodiments, the control circuitry 222 may be included in the nicotine vapor generator assembly 110 instead of the power supply assembly 210. In some example embodiments, the nicotine e-vaping device 100 may be a unitary piece that includes the nicotine vapor generator assembly 110 and the power supply assembly 210 in the unitary piece, instead of including the nicotine vapor generator assembly 110 and the power supply assembly 210 as separate pieces that are coupled together to form the nicotine e-vaping device 100.

As shown in FIGS. 1A-1C, the power supply assembly 210 includes an initialization interface 216 configured to be manually manipulated to cause the control circuitry 222 to cause power to be supplied to the nicotine vapor generator assembly 110. As shown, the initialization interface 216 may be a button device, but example embodiments are not limited thereto. For example, the initialization interface 216 may be a switch device. Still referring to FIGS. 1A-1C, the power supply assembly 210 may include a power supply interface 228 that is configured to connect with an electrical power supply conduit to enable the power supply 220 to be charged or re-charged via power supplied thereto from an external power source via the power supply interface 228. In some example embodiments, the power supply interface 228 may be a Universal Serial Bus (USB) interface, a mini-USB interface, a micro-USB interface, or the like.

In some example embodiments, wherein the nicotine vapor generator assembly 110 and the power supply assembly 210 are configured to be detachably coupled via complementary connector assemblies 142 and 323, respectively, one or more electrical circuits through the nicotine vapor generator assembly 110 and the power supply assembly 210 may be established based on connector assemblies 142, 232 being coupled together. In one example, the one or more established electrical circuits may include at least the nicotine vaporizer assembly 400, the control circuitry 222, and the power supply 220. As shown in at least FIG. 1C, the power supply assembly 210 may include an electrode structure 230 that is electrically coupled to the power supply 220 and the control circuitry 222 via an electrical connection structure 226. As shown, the electrode structure 230 is configured to contact a corresponding electrode structure 172 of the nicotine vaporizer assembly 400 of the nicotine vapor generator assembly 110, based on the connector 323 of the power supply assembly 210 coupling with the connector assembly 142 of the nicotine vapor generator assembly 110, to establish an electrical circuit that includes at least the power supply 220, the control circuitry 222, and the nicotine vaporizer assembly 400 thereby electrically coupling the power supply 220 and control circuitry 222 to the nicotine vaporizer assembly 400. In the example embodiments shown, electrode structures 230 and 172 are configured to contact each other via flush contact of respective surfaces of the electrode structures 230 and 172.

Still referring to FIGS. 1A-1C, the nicotine e-vaping device 100 may include an air inlet 250 that is configured to direct air to be drawn into an interior of the nicotine e-vaping device 100 and one or more conduits configured to direct the air to be drawn into the nicotine vaporizer assembly 400 to entrain nicotine vapor generated therein and to further be drawn out of the nicotine vaporizer assembly 400 and out of the nicotine e-vaping device 100 via the conduits 188-*i*, 160-*i*, 112-*i*, and outlet 251 of the outlet assembly 112. As shown, the air inlet 250 may be an arcuate and/or annular inlet that extends partially or entirely around a circumference of an exterior of the nicotine e-vaping device 100. In the example embodiments shown, the air inlet 250 is defined by a gap between the coupled nicotine vapor generator assembly 110 and the power supply assembly 210, but example embodiments are not limited thereto: the air inlet 250 may be entirely located in, and entirely defined by, the nicotine vapor generator assembly 110 or the power supply assembly 210. As further shown, the power supply assembly 210 may include a structure 224 that at least partially defines one or more conduits extending through an interior of at least the power supply assembly 210 from the air inlet 250 towards the nicotine vaporizer assembly 400.

The power supply assembly 210 further includes an adjustment ring 120 that defines one or more orifices 121, and the adjustment ring 120 may be configured to be rotated, in relation to at least the structure 224, around a longitudinal axis of the power supply assembly 210 to adjustably align one or more differently-sized orifices 121 with at least one air conduit defined by the structure 224 in order to adjustably configure the nicotine e-vaping device 100 to support a particular maximum flow rate of air through the nicotine e-vaping device via flow choking by the orifice 121 that is aligned with the conduit defined by structure 224. In some example embodiments, the adjustment ring 120 may be configured to be rotated to isolate the conduit defined by structure 224, to preclude air from being drawn from the air inlet 250 to the nicotine vaporizer assembly 400.

Still referring to at least FIG. 1C, the structure 224 is coupled to the connector 323 and further defines a space that is configured to be in fluid communication with an inlet conduit 178-*i* of the nicotine vaporizer assembly 440 when the connector 323 is connected to the connector assembly 142 of the nicotine vapor generator assembly 110.

In some example embodiments, the nicotine e-vaping device 100 may be a unitary piece that includes the nicotine vapor generator assembly 110 and the power supply assembly 210 in the unitary piece, such that there is no need to couple the nicotine vapor generator assembly 110 and the power supply assembly 210 together to establish the one or more electrical circuits.

In some example embodiments, the power supply 220 may include a battery. In some examples, the power supply 220 may include a Lithium-ion battery or one of its variants, for example a Lithium-ion polymer battery, or a different type of battery. Further, the power supply 220 may be rechargeable and may include circuitry configured to allow the battery to be chargeable by an external charging device.

In some example embodiments, the power supply 220 may be electrically connected with the nicotine vaporizer assembly 400 by control circuitry 222 based on a signal received at the control circuitry 222 from a sensor of the nicotine e-vaping device 100, an interface of the nicotine e-vaping device 100 (e.g., initialization interface 216), or a combination thereof. To control the supply of electrical power to nicotine vaporizer assembly 400, the control circuitry 222 may execute one or more instances of computer-executable program code. The control circuitry 222 may include a processor and a memory. The memory may be a computer-readable storage medium storing computer-executable code. The control circuitry 222 may be a special purpose machine configured to execute the computer-executable code to control the supply of electrical power to the nicotine vaporizer assembly 400.

Figures 3A, 3B:
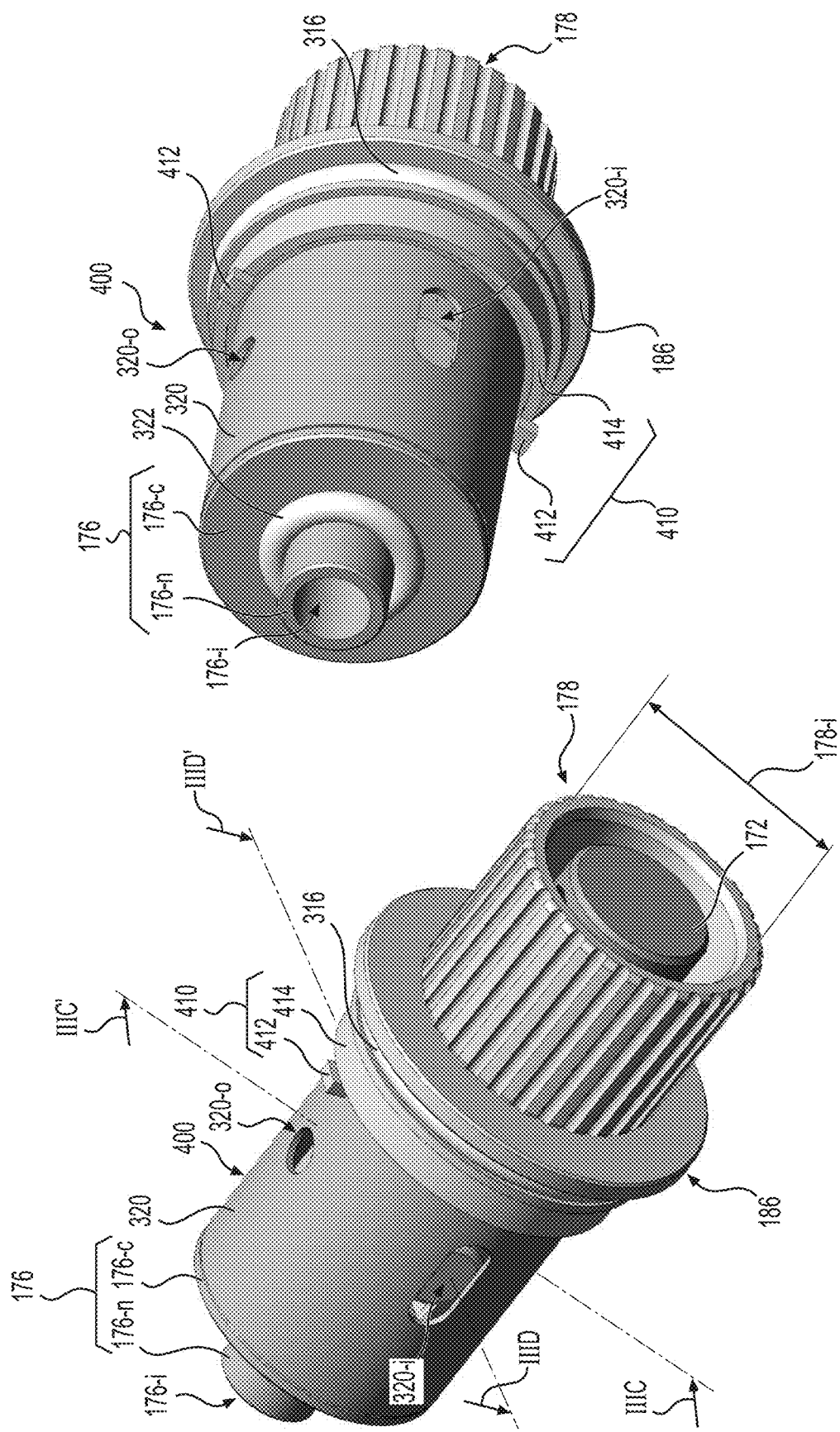
FIGS. 3A-3B are perspective views of a nicotine vaporizer assembly according to some example embodiments.

Referring now to FIGS. 3A-3D, the nicotine vaporizer assembly 400 is now described. FIGS. 3A-3B are perspective views of a nicotine vaporizer assembly according to some example embodiments. FIG. 3C is a cross-sectional perspective view along line IIIC-IIIC' of the nicotine vaporizer assembly of FIGS. 3A-3B according to some example embodiments. FIG. 3D is a cross-sectional perspective view along line IIID-IIID' of the nicotine vaporizer assembly of FIGS. 3A-3B according to some example embodiments.

Referring to FIGS. 3A-3D, a nicotine vaporizer assembly 400 may include a conduit structure 186, a nicotine vaporizer 180 that includes a dispensing interface 180-W and a heating element 180-H, an electrode structure 172, and an outlet conduit structure 176. The conduit structure 186 has an inner surface 186-s that at least partially defines a conduit 174 extending through the nicotine vaporizer assembly 400 along a longitudinal axis 401 thereof. The conduit structure 186 may further include a set of slots 388, extending coaxially to the longitudinal axis 401, that are configured to structurally support the dispensing interface 180-W and hold the dispensing interface 180-W in place in a fixed position in relation to the conduit structure 186. As shown, an interface between the conduit structure 186 and the outer housing 130 may be sealed with a ring gasket 316.

As shown, the dispensing interface 180-W may extend transversely through the conduit 174, between slots 388 extending along opposite sides of the conduit 174. As further shown, a heating element 180-H may extend around an outer surface of the dispensing interface 180-W. As shown, the heating element 180-H may be a wire coil that is wrapped around the dispensing interface 180-W in direct contact therewith. The dispensing interface 180-W may include one or more instances of wicking material and may be referred to as a wick.

As shown in FIGS. 3A-3D, electrode structure 172 may be positioned at a first end of the conduit structure 186 by gasket 173. The electrode structure 172 and gasket 173 may collectively define a first end of the conduit 174 along the longitudinal axis 401. As shown, the electrode structure 172 includes a central conduit 172-i that extends along ("coaxially to") the longitudinal axis 401 and a set of at least two inlet conduits 172-o that extend transversely, orthogonally to the longitudinal axis 401, between a first end of the central conduit 172-i and an exterior of the electrode structure 172 that is further exterior to the conduit 174. Accordingly, as shown in at least FIGS. 3C-3D, the central conduit 172-i has a first end that is in fluid communication with an exterior of the nicotine vaporizer assembly 400, independently of conduit 174, via the transversely-extending inlet conduits 172-o, and an opposite, second end that is directly exposed to the conduit 174. Thus, the electrode structure 172 is configured to direct a fluid, such as air, drawn into the nicotine vaporizer assembly 400 to be drawn into the central conduit 172-i from an exterior via one or more inlet conduits 172-o and to be further drawn from the central conduit 172-i into the conduit 174. The gasket 173 may include an electrically insulating material, such that the gasket 173 electrically insulates the electrode structure 172 and the conduit structure 186 from each other.

Figure 6B:
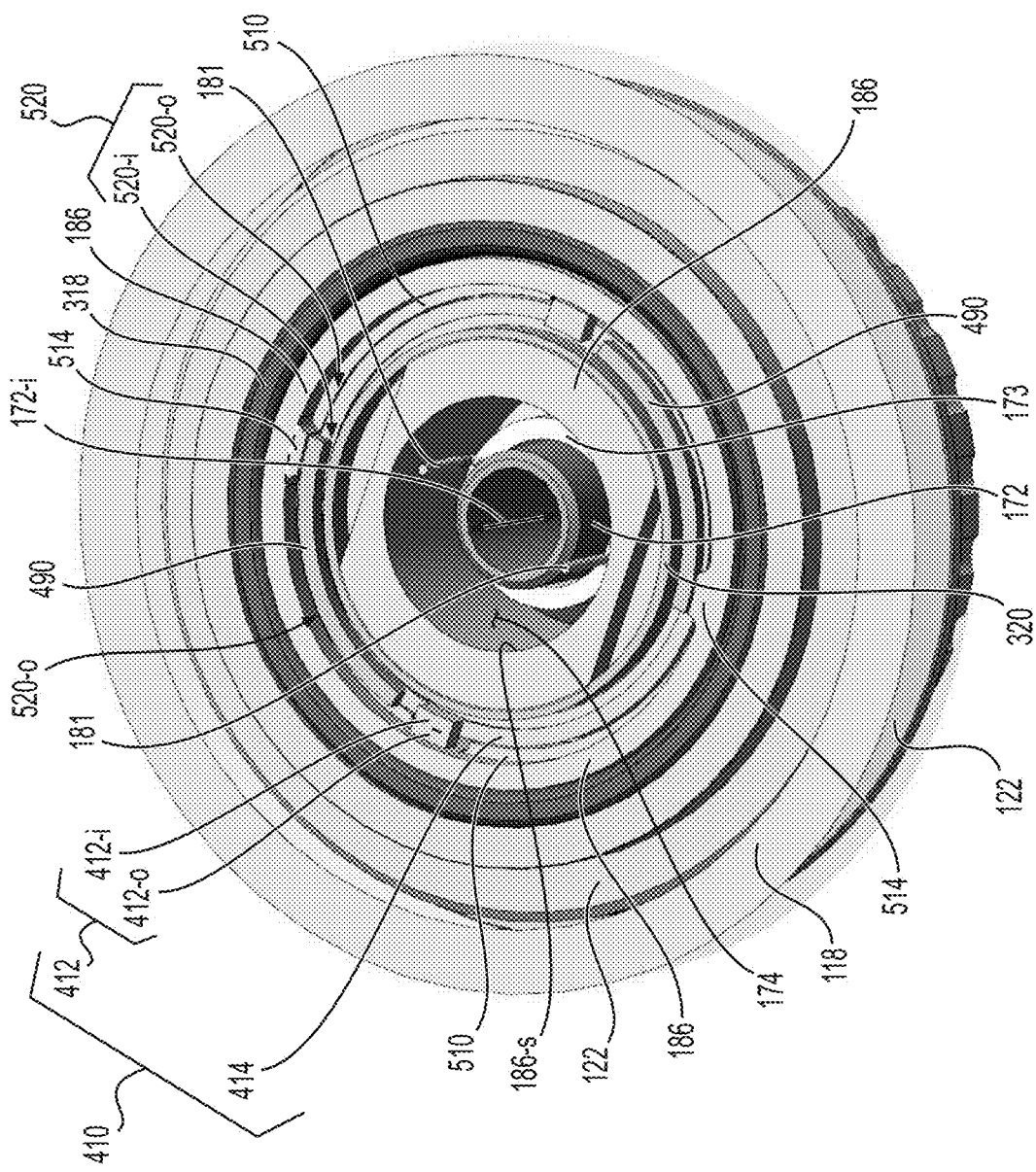
FIG. 6B is a cross-sectional view of the nicotine vapor generator assembly of FIG. 6A along view line VIB-VIB' according to some example embodiments.

As further shown in FIGS. 3C-3D, the nicotine vaporizer assembly 400 includes a set of two electrical leads 181 (only one electrical lead 181 is shown in FIGS. 3C-3D, but both electrical leads 181 are shown in FIG. 6B) that are connected to opposite ends of the heating element 180-H. One electrical lead 181, connected to one end of the heating element 180-H, may be connected to the electrode structure 172 and may extend thereto via a portion of the conduit 174 and through a portion of the gasket 173. Another electrical lead 181, connected to an opposite end of the heating element 180-H, may be connected to the conduit structure 186 and may extend thereto via a portion of the conduit 174 and through a portion of the gasket 173. As a result, the electrical leads 181 may electrically couple the opposite ends of the heating element 180-H with the electrode structure 172 and the conduit structure 186, respectively. The gasket 173 may include an electrically insulating material, such that the gasket 173 may electrically insulate the leads 181 extending through the gasket 173 from each other and may further electrically insulate the electrode structure 172 and the conduit structure 186 from each other. Accordingly, the electrode structure 172 may be configured to be an anode or cathode, and the conduit structure 186 may be configured to be an opposite thereof (e.g., a cathode or anode). As shown in FIG. 1C, a lower surface 186-H of the conduits structure 186 may be configured to contact a portion of the power supply assembly 210 when the nicotine vapor generator assembly 110 is coupled to the power supply assembly 210. In particular, the lower surface 186-H of the conduit structure 186 is configured to contact the connector assembly 232 of the power supply assembly 210 when the nicotine vapor generator assembly 110 is coupled to the power supply assembly 210, concurrently with a surface of the electrode structure 172 contacting the electrode structure 230 of the power supply assembly 210. Accordingly, the nicotine vaporizer assembly 400 is configured to establish an electrical circuit that extends therethrough when the nicotine vapor generator assembly 110 is coupled to the power supply assembly 210, where the electrical circuit extends from the power supply 220 to the electrode structure 230 via the control circuitry 222, from the electrode structure 230 to the electrode structure 172 that is in contact with the electrode structure 230, from the electrode structure 172 to a first end of the heating element 180-H via a first electrical lead 181 that is in contact with both the first end of the heating element 180-H and the electrode structure 172, through the heating element 180-H from the first end to an opposite second end thereof, from the second end of the heating element 180-H to the conduit structure 186 via a second electrical lead 181 that is in contact with both the second end of the heating element 180-H and the conduit structure 186, and from the conduit structure 186 to the power supply 220 via at least the connector assembly 232.

Still referring to FIGS. 3A-3D, the nicotine vaporizer assembly 400 includes a sheath structure 178 that surrounds a first end of the electrode structure 172 that is isolated from the conduit 174 by at least the gasket 173 and conduit structure 186. The sheath structure 178 extends coaxially with the electrode structure 172 and surrounds the first end of the electrode structure 172 as shown in FIGS. 3C-3D to define an annular inlet conduit 178-i that extends coaxially to the longitudinal axis 401 and is defined by the gasket 173, the conduit structure 186, an inner surface of the sheath structure 178, and an outer surface of the electrode structure 172. As shown, the inlet conduit 178-*i* is open to an exterior of the nicotine vaporizer assembly 400 and is further open to the inlet conduits 172-*i* of the electrode structure 172. Accordingly, the nicotine vaporizer assembly 400 is configured to direct a fluid, such as air, that is drawn into the nicotine vaporizer assembly 400 to be drawn into the inlet conduits 172-*i* via the inlet conduit 178-*i*. The sheath structure 178 may further provide protection to the electrode structure from impacts at least partially orthogonally to the longitudinal axis 401, thereby improving the durability of the nicotine vaporizer assembly 400.

Still referring to FIGS. 3A-3D, the nicotine vaporizer assembly 400 includes an outlet conduit structure 176 that defines an outlet conduit 176-*i* and a longitudinal end of the conduit 174. The nicotine vaporizer assembly further includes an outer housing 320 that extends coaxially to the longitudinal axis 401, between a surface of the conduit structure 186 and the outlet conduit structure 176.

Referring first to the outer housing 320, the outer housing 320 includes first ports 320-*o* that extend through the outer housing 320 and are spaced apart on opposite sides of the outer housing 320 (e.g., are offset by 180 degrees from each other. The outer housing 320 further includes second ports 320-*i* that extend through the outer housing 320 and are spaced apart on opposite sides of the outer housing 320 (e.g., are offset by 180 degrees from each other), where the first ports 320-*o* and the second ports 320-*i* are orthogonal to each other around the outer housing 320 (e.g., the second ports 320-*i* and the first ports 320-*o* are offset by 90 degrees from each other). As shown, an inner surface of the outer housing 320 and an outer surface of the conduit structure 186 define the inner and outer radial boundaries of an annular conduit 321 that extends coaxially to longitudinal axis 401 between a surface of the conduit structure 186 and the outlet conduit structure 176. Each port of the first ports 320-*o* and the second ports 320-*i* may establish fluid communication between the dispensing interface 180-W and an exterior of the nicotine vaporizer assembly 400 via annular conduit 321. As shown in at least FIGS. 9A-9E, one or more of the ports 320-*o* and 320-*i* may be exposed to the reservoir 119 of the reservoir assembly 114, either directly or via one or more ports 132, 188-*o* radially aligned with the one or more of the ports 320-*o* and 320-*i*, such that one or more of the ports 320-*o* and 320-*i* may be configured to establish fluid communication between the dispensing interface 180-W and the reservoir 119 when the nicotine vaporizer assembly 400 is coupled to the reservoir assembly 114 and the isolation structure 188 is rotated to expose at least the barrel conduit 188-*a* to the reservoir 119. Accordingly, the nicotine vaporizer assembly 400 may be configured to direct nicotine pre-vapor formulation from the reservoir 119 to the dispensing interface 180-W via one or more ports 320-*o*, 320-*i* and via the annular conduit 321, to which opposite ends of the dispensing interface 180-W are directly exposed as shown in FIGS. 3C-3D.

In some example embodiments, the nicotine vaporizer assembly 400 may include an additional dispensing interface occupying a portion or an entirety of the annular conduit 321, such that the annular dispensing interface isolates the dispensing interface 180-W from direct exposure to the one or more ports 320-*o*, 320-*i* (e.g., where only empty space interposes between the dispensing interface 180-W and the one or more ports 320-*o*, 320-*i*), and the additional dispensing interface may enable nicotine pre-vapor formulation to be drawn from the one or more ports 320-*o*, 320-*i* to the dispensing interface 180-W through an interior of the additional dispensing interface. As further shown in FIGS. 3C-3D, the longitudinal axis of the dispensing interface 180-W may be radially aligned with the second ports 320-*o*.

The outlet conduit structure 176 may include a plate structure 176-*c* that at least partially defines a longitudinal end of the conduits 174, 321 and a conduit structure 176-*n*, aligned with the longitudinal axis 401 and extending coaxially therewith, that defines the outlet conduit 176-*i* that itself establishes fluid communication between the proximate longitudinal end of conduit 174 and the exterior of the nicotine vaporizer assembly 400. A fluid that is located in the conduit 174, including air drawn into the conduit 174 via conduits 178-*i*, 172-*i*, and 172-*o*, a nicotine vapor generated in the conduit 174 based on the heating element 180-H heating nicotine pre-vapor formulation drawn into the dispensing interface 180-W from the reservoir 119, or a combination thereof, may be drawn out of the conduit 174 and out of the nicotine vaporizer assembly 400 via the outlet conduit 176-*i*.

Referring back to at least FIGS. 1C and 2C-2D, the nicotine vaporizer assembly 400 and reservoir assembly 114 may be configured to be coupled with each other such that the nicotine vaporizer assembly 400 is inserted into the conduits 188-*i* and 188-*a*, where longitudinal axes 401 and 201 are aligned to be the same longitudinal axis, such that the nose structure 176-*n* of the nicotine vaporizer assembly 400 extends through conduit 188-*i*, at least partially sealed therewith via at least a portion of the outer housing 320 occupies barrel conduit 188-*a*, and one or more of the ports 320-*o*, 320-*i* is radially aligned with the one or more ports 132. As shown in FIGS. 2C-2D, the inner housing 130 is configured to enable the nicotine vaporizer assembly 400 to be inserted into the conduit 188-*a*, 188-*i*, such that an outlet conduit 176-*i* of the nicotine vaporizer assembly 400 is in direct fluid communication with conduit 160-*i*, such that conduits 176-*i*, 160-*i* collectively define an outlet conduit that extends from conduit 174 to an exterior of the reservoir assembly 114 and, via the outlet conduit 112-*i* and outlet 251, to an exterior of the nicotine vapor generator assembly 110. The isolation structure 188 may rotate around longitudinal axis 201 to adjustably expose the one or more ports 320-*o*, 320-*i* to the reservoir 119 via the one or more ports 132 based on adjustably radially aligning the one or more ports 188-*o* with the one or more ports 132 and thus the one or more ports 320-*o*, 320-*i*.

Figures 5A, 5B:
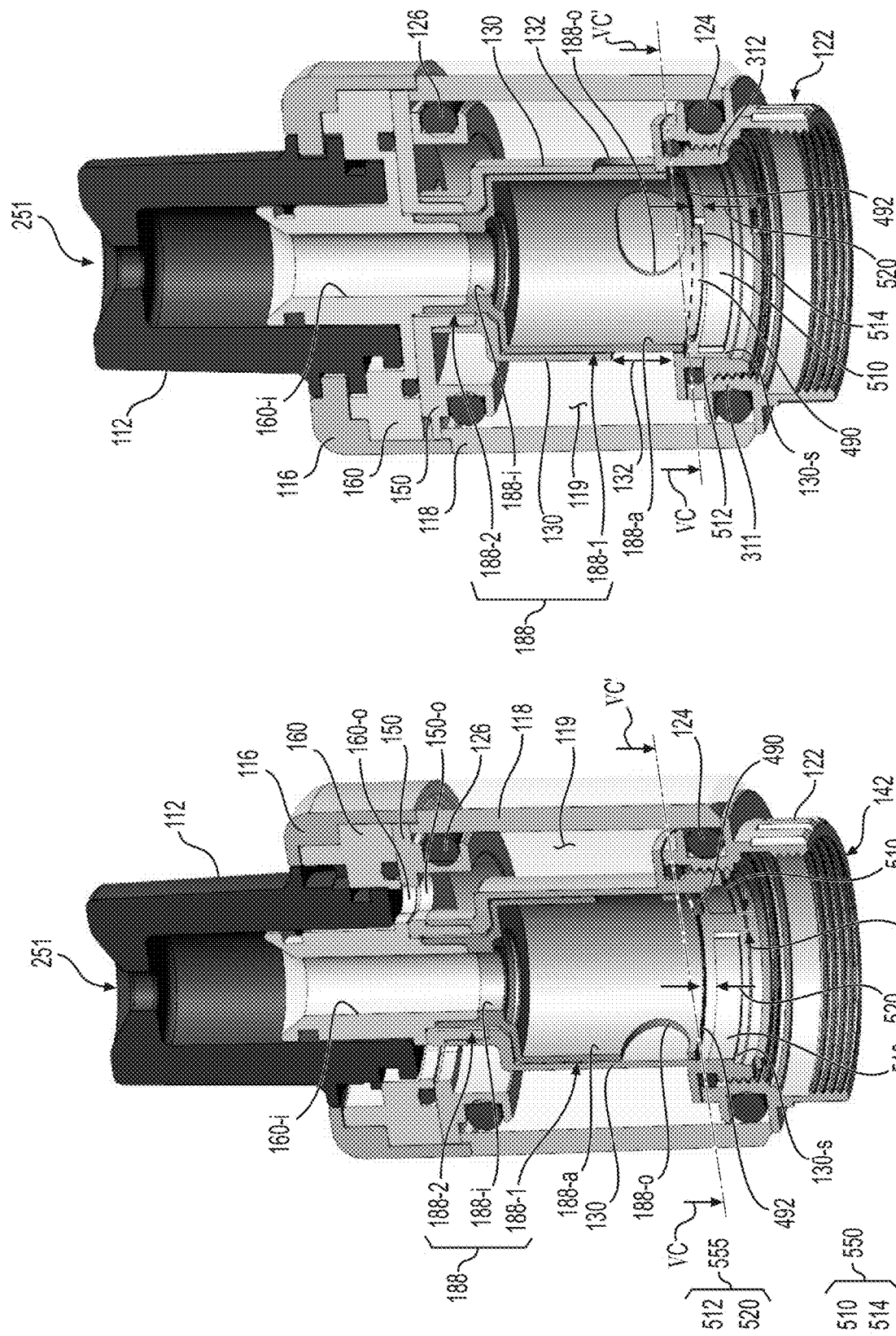
FIG. 5A is a cross-sectional view along line IIC-IIC' of the nicotine vapor generator assembly of FIGS. 2A-2B according to some example embodiments.
FIG. 5B is a cross-sectional view along line IID-IID' of the nicotine vapor generator assembly of FIGS. 2A-2B according to some example embodiments.
Figure 5C:
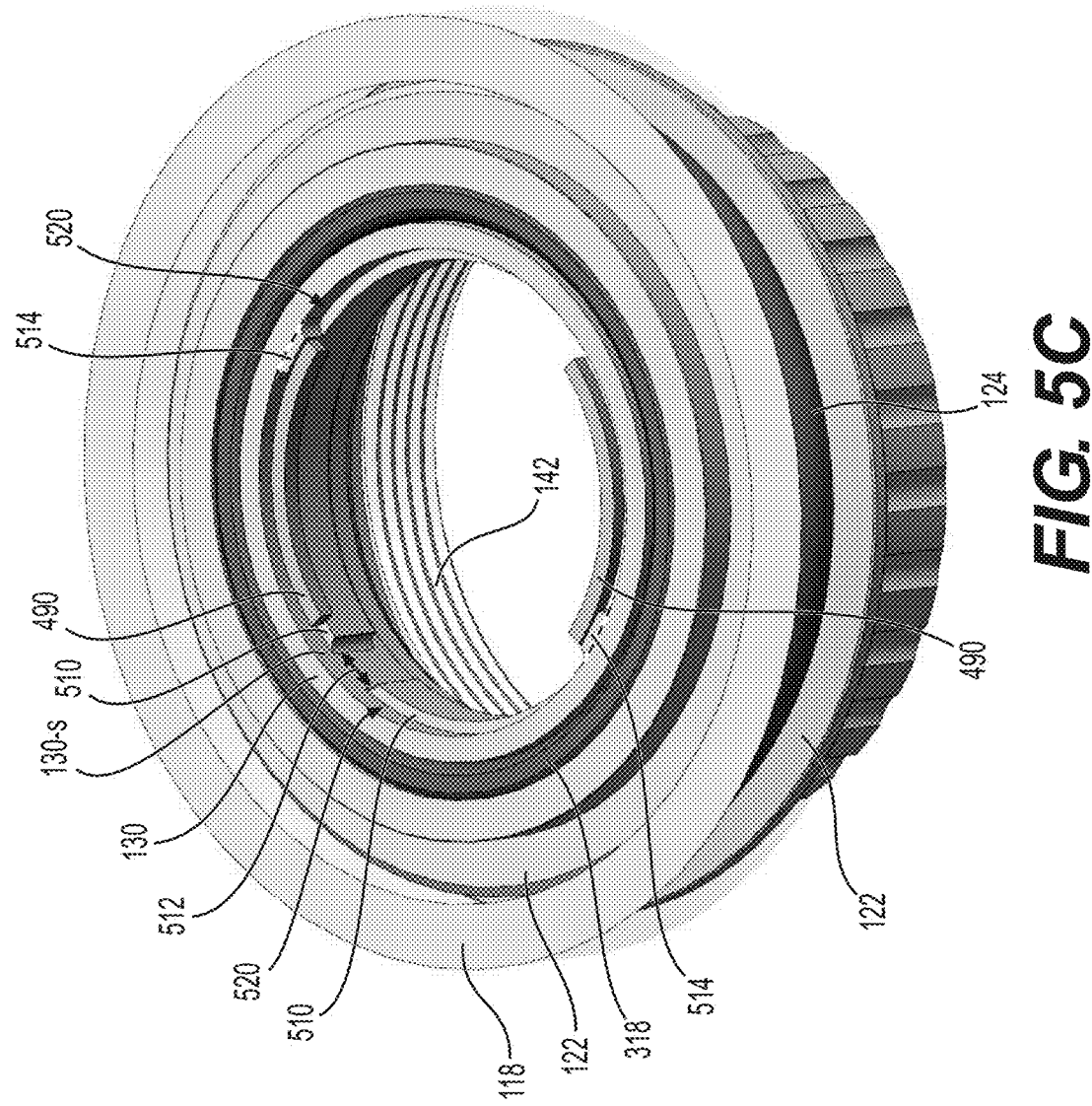
FIG. 5C is a cross-sectional perspective view along line VC-VC' of the reservoir assembly of FIGS. 5A-5B according to some example embodiments.

FIG. 4 is a perspective view of an isolation structure according to some example embodiments. FIG. 5A is a cross-sectional view along line IIC-IIC' of the nicotine vapor generator assembly of FIGS. 2A-2B according to some example embodiments. FIG. 5B is a cross-sectional view along line IID-IID' of the nicotine vapor generator assembly of FIGS. 2A-2B according to some example embodiments. FIG. 5C is a cross-sectional perspective view along line VC-VC' of the reservoir assembly of FIGS. 5A-5B according to some example embodiments. FIG. 6A is a cross-sectional view of the nicotine vapor generator assembly of FIGS. 2A-2B according to some example embodiments. FIG. 6B is a cross-sectional view of the nicotine vapor generator assembly of FIG. 6A along view line VIB-VIB' according to some example embodiments.

As shown in FIGS. 5A-5C, the inner housing 130 includes projection structures 510 that extend partially around an inner surface 130-*s* of the inner housing 130 and are radially spaced apart to define one or more longitudinal conduits 512, each longitudinal conduit 512 extending coaxially with longitudinal axis 201 between adjacent projection structures 510. As shown in FIG. 4, the isolation structure 188 may include a projection structure 490 that extends from the lower edge 492 of the isolation structure 188, where the extension is coaxial with the longitudinal axis 201. As shown, each projection structure 490 may extend around a limited portion of the lower edge 492 of the isolation structure 188. For example, in the illustrated example embodiments, each projection structure 490 extends about 90 degrees around the circumference of the lower edge 492, and the two projection structures 490 are offset by 90 degrees from each other, such that each projection structure 490 extends around ¼ of the lower edge 492 of the isolation structure 188 and the two projection structures 490 collectively extend around ½ of the lower edge 492 of the isolation structure 188.

As further shown in FIGS. 5A-5C, a bottom edge 492 of the isolation structure 188 and top edges of the projection structures 510 may collectively define one or more annular conduits 520. As further shown, the projection structures 510 may each include a longitudinal projection structure 514 that isolates separate annular conduits 520 from each other.

Still referring to FIGS. 5A-5C, and further referring to at least FIG. 6A, the annular conduit 520 defined by at least the inner housing 130 and the isolation structure 188 may include an outer annular conduit 520-$o$ and an inner annular conduit 520-$i$, where the outer annular conduit 520-$o$ is defined by the inner housing 130 and the projection structure 510, and the inner annular conduit 520-$i$, which is concentric with the outer annular conduit 520-$o$, is defined by the lower edge 492 of the isolation structure 188. The isolation structure 188 is configured to rotate around longitudinal axis 201 such that the interlock projection structures 490 are restricted to moving through the inner annular conduit 520-$i$ based on rotation of the isolation structure 188 around the longitudinal axis 201.

In some example embodiments, the structures defining conduits 512 and 520 (e.g., projection structures 510 and 514), may collectively define a reservoir assembly connector assembly 550 of the reservoir assembly 114 that is a channel bayonet connector and which is configured to engage with a complementary plug bayonet connector of the nicotine vaporizer assembly 400 to couple the nicotine vaporizer assembly 400 with the reservoir assembly 114 in such a way so as to radially align one or more ports 320-$i$, 320-$o$ with at least the ports 132 of the inner housing 130. The conduits 512 and 520 that are open to each other may be referred to herein as a connector conduit 555 that is defined by the reservoir assembly connector assembly 550.

Figure 3E:
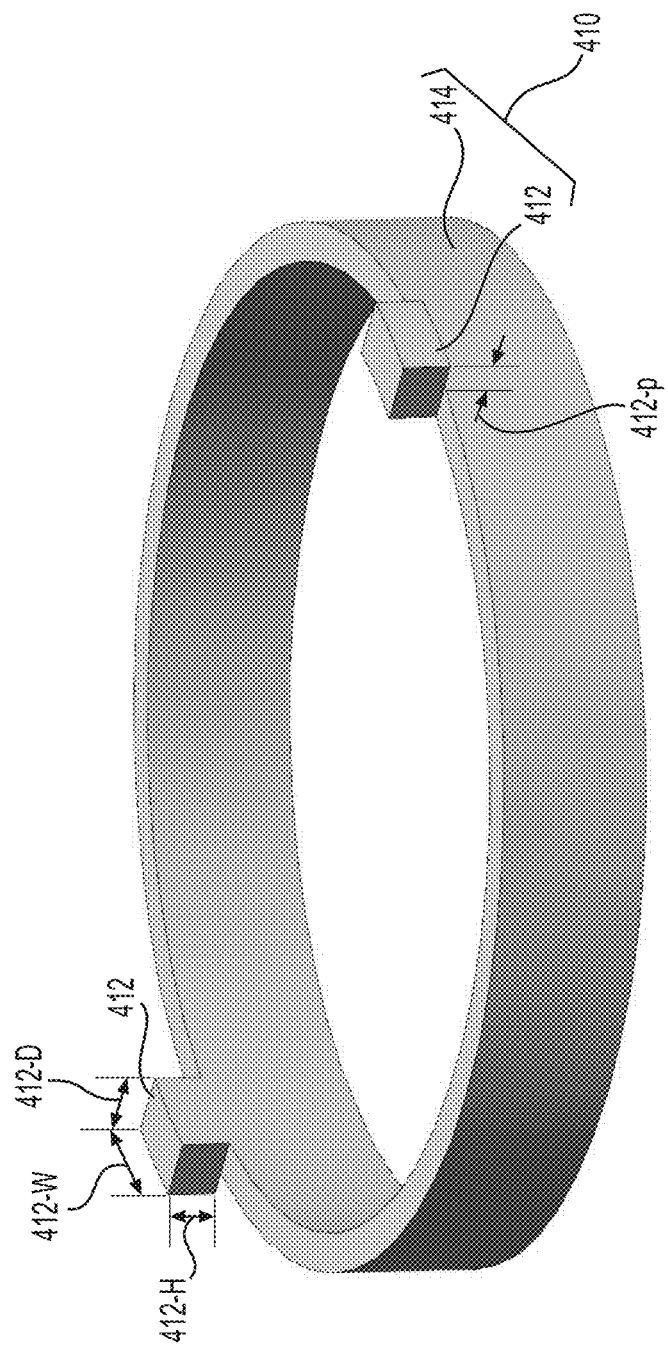
FIG. 3E is a perspective view of an interlock structure according to some example embodiments.

FIG. 3E is a perspective view of an interlock structure according to some example embodiments. The interlock structure 410 shown in FIG. 3E may be the interlock structure 410 shown in FIGS. 3A-3D. The interlock structure 410 may partially or entirely comprise a plug bayonet connector of the nicotine vaporizer assembly 400 that is complementary with the aforementioned channel bayonet connector of the reservoir assembly 114.

As shown in FIG. 3E, the interlock structure 410 may include a ring structure 414 that is configured to extend around the outer housing 320 of the nicotine vaporizer assembly 400. In some example embodiments, the ring structure 414 is configured to be fixed in place in relation to the outer housing 320 and/or the conduit structure 186 (e.g., via adhesive, welding, one or more connectors, or the like). The interlock structure 410 may further include a connector structure 412 that is configured to engage with the complementary channel bayonet connector of the reservoir assembly 114 (e.g., one or more conduits 512 and one or more conduits 520) to couple the nicotine vaporizer assembly 400 with the reservoir assembly 114. As shown, the connector structure 412 may be a plug bayonet connector structure that is configured to engage with a corresponding, complementary bayonet connector structure of the reservoir assembly connector assembly 550. As shown, the connector structure 412 may be a plug structure that extends a distance 412-H away from the ring structure 414 in a longitudinal direction, has a width 412-W, has a depth 412-D, and projects a distance 412-P away from the ring structure 414 in a radial direction. While the connector structure 412 is shown in FIG. 3E to be a plug bayonet connector, it will be understood that example embodiments are not limited thereto, and the connector structure 412 may be any type of connector, including a channel bayonet connector structure, a pin connector structure, a threaded connector structure, some combination thereof, or the like.

Figure 8B:
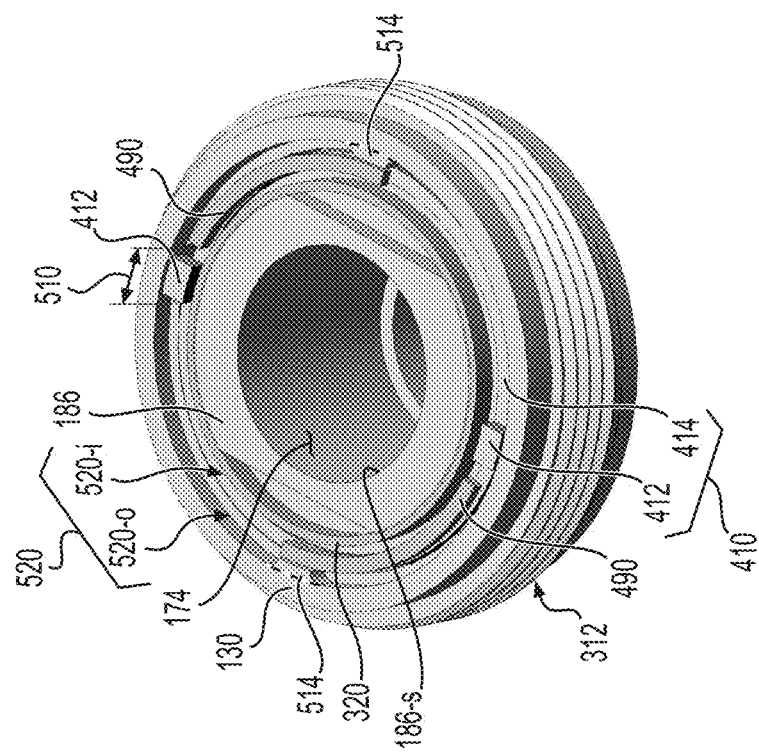
FIG. 8B is a cross-sectional perspective view along line VIIIB-VIIIB' of the reservoir assembly and nicotine vaporizer assembly of FIG. 8A according to some example embodiments.
Figure 8A:
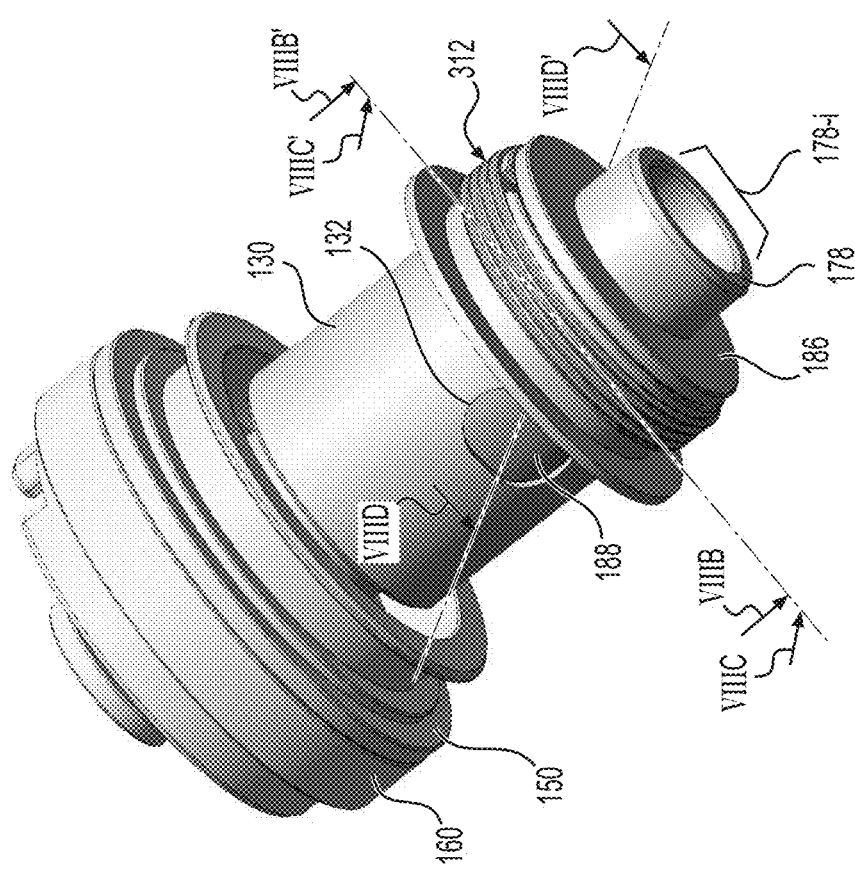
FIG. 8A is a perspective view of a reservoir assembly and a nicotine vaporizer assembly inserted into the reservoir assembly according to some example embodiments.
Figures 9A, 9B:
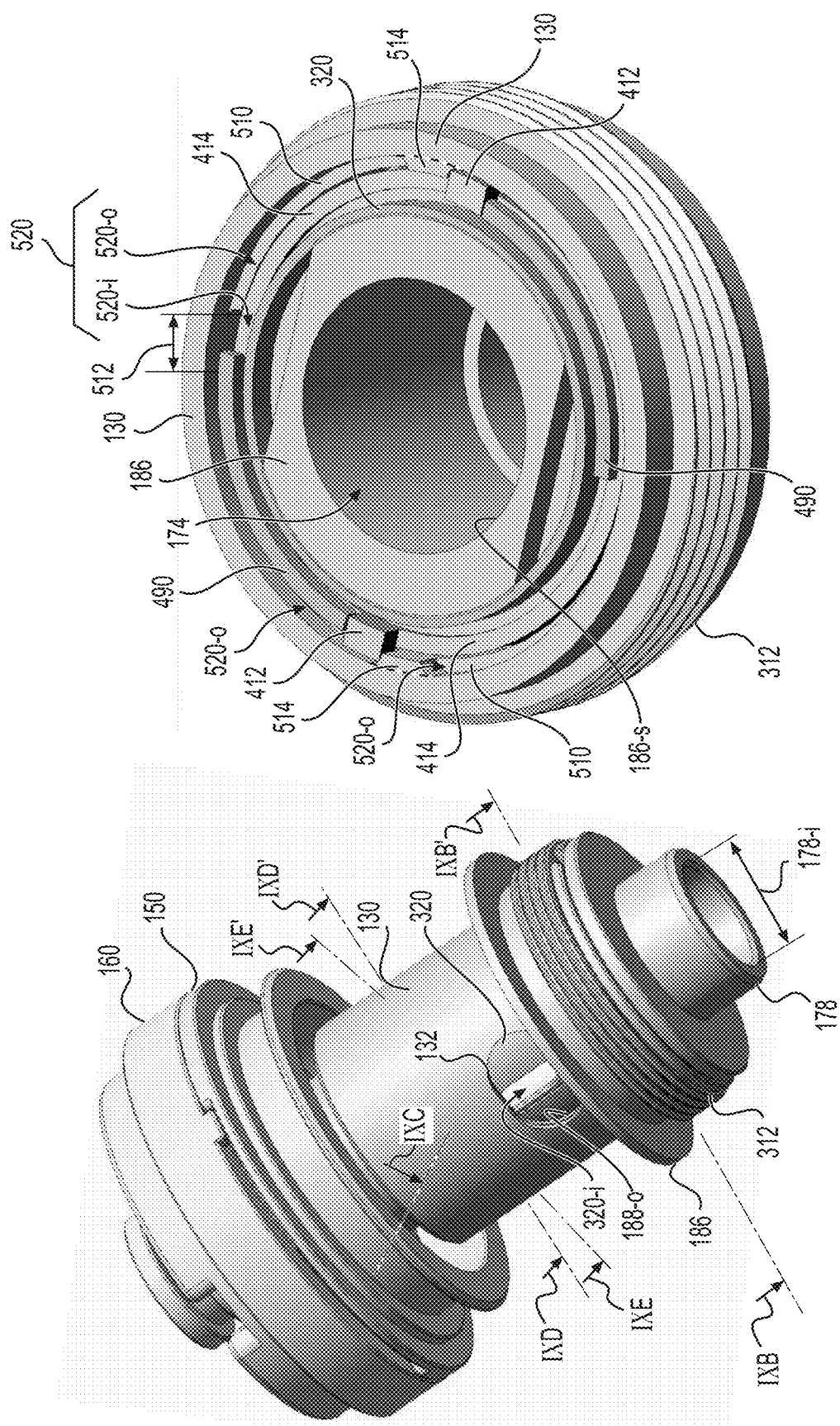
FIG. 9A is a perspective view of a reservoir assembly and a nicotine vaporizer assembly locked into the reservoir assembly according to some example embodiments.
FIG. 9B is a cross-sectional perspective view along line IXB-IXB' of the reservoir assembly and nicotine vaporizer assembly of FIG. 9A according to some example embodiments.

FIG. 7A is a perspective view of a reservoir assembly and a nicotine vaporizer assembly aligned with the longitudinal axis of the reservoir assembly according to some example embodiments. FIG. 7B is a cross-sectional view of the reservoir assembly and aligned nicotine vaporizer assembly of FIG. 7A along view line VIIB-VIIB'. FIG. 8A is a perspective view of a reservoir assembly and a nicotine vaporizer assembly inserted into the reservoir assembly according to some example embodiments. FIG. 8B is a cross-sectional perspective view along line VIIIB-VIIIB' of the reservoir assembly and nicotine vaporizer assembly of FIG. 8A according to some example embodiments. FIG. 8C is a cross-sectional view along line VIIIC-VIIIC' of the reservoir assembly and nicotine vaporizer assembly of FIG. 8A according to some example embodiments. FIG. 8D is a cross-sectional view along line VIIID-VIIID' of the reservoir assembly and nicotine vaporizer assembly of FIG. 8A according to some example embodiments. FIG. 9A is a perspective view of a reservoir assembly and a nicotine vaporizer assembly locked into the reservoir assembly according to some example embodiments. FIG. 9B is a cross-sectional perspective view along line IXB-IXB' of the reservoir assembly and nicotine vaporizer assembly of FIG. 9A according to some example embodiments. FIG. 9C is a cross-sectional view along line IXC-IXC' of the reservoir assembly and nicotine vaporizer assembly of FIG. 9A according to some example embodiments. FIG. 9D is a cross-sectional view along line IXD-IXD' of the reservoir assembly and nicotine vaporizer assembly of FIG. 9A according to some example embodiments. FIG. 9E is a cross-sectional view along line IXE-IXE' of the reservoir assembly and nicotine vaporizer assembly of FIG. 9A according to some example embodiments.

Referring now to at least FIGS. 6A-9E, when the nicotine vaporizer assembly 400 is inserted into the reservoir assembly 114 to at least partially occupy the conduits 188-$i$ and 188-$a$, the interlock structure 410 may be configured to establish a bayonet connection between the nicotine vaporizer assembly 400 and the reservoir assembly 114 based on interaction between the interlock structure 410 and the conduits 512, 520 of the reservoir assembly connector assembly 550. As shown in FIGS. 6A-8C, the nicotine vaporizer assembly 400 may be inserted into reservoir assembly 114, through connector assembly 142 and into the conduits 188-$i$, 188-$a$, where the connector structures 412 are radially aligned with separate respective conduits 512 of the connector assembly 550, such that the projector structures 412 move, coaxially in relation to the longitudinal axis 201, through the separate, respective conduits 512 and into separate respective conduits 520 as the nicotine vaporizer assembly 400 is inserted into the conduits 188-$i$, 188-$a$.

As shown in FIGS. 8A-9E, once the nicotine vaporizer assembly 400 is inserted longitudinally into the reservoir assembly 114 such that the connector structures 412 are inserted longitudinally into separate, respective conduits 520 via conduits 512, the nicotine vaporizer assembly 400 may be rotated around the longitudinal axis 201 (which may be aligned with longitudinal axis 401 to be the same longitudinal axis based on the nicotine vaporizer assembly 440 being inserted into the reservoir assembly 114) such that the connector structures 412 move in separate, respective arcs around longitudinal axis 201 and through separate, respective conduits 520 to impinge upon separate, respective structures 514 that restrict further motion of the projector structures 412 away from the respective conduits 512 that are directly open to the respective conduits 520 in which the connector structure 412 are located. Such motion of the connector structure 412 to impinge upon separate, respective structure 514 may correspond with the nicotine vaporizer assembly 400 being rotated around longitudinal axis 201 to radially align one or more sets of ports 320-*o*, 320-*i* with ports 132.

As shown in at least FIGS. 6A-6C, the projector structures 412 each include an inner portion 412-*i* that is longitudinally aligned with the ring structure 414 and an outer portion 412-*o* that projects radially from the ring structure 414. Referring back to FIGS. 7A-9E, the connector structure 412 is configured to be inserted into a conduit 520, and move therethrough, such that the inner portion 412-*i* is in the inner annular conduit 520-*i* of the given conduit 520 and the outer portion 412-*o* is in the outer annular conduit 520-*o* of the given channel. Furthermore, the connector structure 412 may be configured such that the outer portion 412-*o* is confined to moving through the outer annular conduit 520-*o* and the inner portion 412-*i* is confined to moving through the inner annular conduit 520-*i* when the connector structure 412 is moving through a conduit 520.

As further shown in FIGS. 8A-9E, the nicotine vapor generator assembly 110 is configured to enable the isolation structure 188 to rotate around the longitudinal axis 201 such that the projection structure 490 moves through the inner annular conduit 520-*i* to selectively obstruct the inner annular conduit 520-*i* between a structure 514 and a conduit 512, to isolate at least the inner portion 412-*i* of the connector structure 412, that is impinging upon the structure 514, from the conduit 512. As a result, the projection structure 490 may restricting at least a portion of the interlock structure 410 (e.g., inner portion 412-*i*) from being disengaged from the bayonet connection defined by conduits 512, 520, based on at least a conduit and/or series of conduits through which at least a portion 412-*i* of the interlock structure 410 may move to disengage the nicotine vaporizer assembly 400 from the reservoir assembly 114 being obstructed by the projection structure 490.

As shown in at least FIGS. 8A-9E, the isolation structure 188 is configured to expose at least inner annular conduit 520-*i* to a conduit 512 based on the isolation structure 188 being in a position that radially mis-aligns one or more ports 188-*o* with one or more ports 132 to isolate the barrel conduit 188-*a* from the one or more ports 132. Accordingly, the reservoir assembly 114 may be configured to enable a nicotine vaporizer assembly 400 to be removably coupled with the reservoir assembly 114, via engagement of the interlock structure 410 and the connector assembly 550 to cause one or more connector structure 412 to move through one or more sets of conduits 512, 520 to impinge upon a structure 514, based on the isolation structure 188 being in a first position in which the isolation structure 188 isolates the reservoir 119 from the nicotine vaporizer assembly 400 and in which the isolation structure 188 does not isolate conduits 520, 512 from each other to enable the nicotine vaporizer assembly 400 to be inserted longitudinally into the reservoir assembly 114 and rotated around the longitudinal axis 201 such that the connector structure 412 of the interlock structure 410 of the nicotine vaporizer assembly 440 moves through a conduit 512 and a conduit 520 that is open to the conduit 512 to impinge upon a structure 514, such that one or more ports 320-*o*, 320-*i* of the nicotine vaporizer assembly 400 are radially aligned with the one or more ports 132 when the one or more projector structures 412 are impinging upon separate, respective structures 514.

As further shown in FIGS. 8A-9E, the reservoir assembly 114 may be configured to enable a nicotine vaporizer assembly 400 to be restricted from being decoupled from the reservoir assembly 114 based on the isolation structure 188 being in a second position in which the isolation structure 188 radially aligns the one or more ports 188-*o* thereof with the one or more ports 132 of the inner housing 130 and the one or more ports 320-*o*, 320-*i* of the nicotine vaporizer assembly 400 such that the isolation structure 188 exposes the nicotine vaporizer assembly 400 to the reservoir 119 and in which the isolation structure 188 also obstructs a portion of the inner annular conduit 520-*i* that is between the connector structure 412 (impinging on structure 514) and the conduit 512, thereby restricting the connector structure 412 from being moved through the conduit 520 to the conduit 512 and therethrough to an exterior of the reservoir assembly 114, thereby restricting the interlock structure 410 from disengaging from the reservoir assembly 114 when the conduit 188-*a*, and thus the nicotine vaporizer assembly 400 held therein, is exposed to the reservoir 119 via the one or more ports 188-*o* and radially aligned one or more ports 132.

Accordingly, the isolation structure 188 may be configured to partially or entirely mitigate leaking of nicotine pre-vapor formulation from reservoir 119 to an exterior of the reservoir assembly 114 in the absence of nicotine vaporizer assembly 400 being coupled to the reservoir assembly 114, as the isolation structure 188 is configured to isolate the reservoir 119 from the space 188-*a* in which the nicotine vaporizer assembly 400 is configured to be inserted based on being in a first position that is configured to enable the nicotine vaporizer assembly 400 to be removable engaged with the reservoir assembly 114 and is configured to expose the reservoir 119 with the nicotine vaporizer assembly 400 based on the isolation structure 188 being in a second position that is configured to restrict the nicotine vaporizer assembly 400 from being disengaged from the reservoir assembly 114 based on the isolation structure 188 isolating a portion of conduits 520 from adjacent conduits 512 to restrict the nicotine vaporizer assembly 400 from being rotated around the longitudinal axis 201, based on restricting the connector structure 412 of the interlock structure 410 of the nicotine vaporizer assembly 400 that are impinged upon structures 514 from moving through respective channels (obstructed by respective interlock structures 491 of the isolation structure 188) to respective conduits 512.

In view of the above, it will be understood that the reservoir assembly connector assembly 550 may be configured to detachably couple with the nicotine vaporizer assembly 400 to establish fluid communication between the nicotine vaporizer assembly 400 and a reservoir defined by the reservoir assembly 114 based on a connector element of the nicotine vaporizer assembly 400 engaging with the connector conduit 555 of the nicotine vaporizer connector assembly, where the connector element may be at least the connector structure 412 of the interlock structure 410 of the nicotine vaporizer assembly 400. It will further be understood that the reservoir assembly 114 may include an isolation structure 188 configured to move, in relation to both the reservoir assembly 114 and the reservoir assembly connector assembly 550, between a first position, shown in FIGS. 9A-9E, where the isolation structure 188 exposes the nicotine vaporizer assembly 400 to the reservoir 119 and at least partially obstructs the connector conduit, defined by at least one conduit 512 and a conduit 520 that is open to the at least one conduit 512, to restrict the connector element from disengaging from the connector conduit 520, and a second position, shown in FIGS. 8A-8C, where the isolation structure 188 isolates the nicotine vaporizer assembly 400 from the reservoir 119 and opens the connector conduit 555 to enable the connector element to disengage from the connector conduit 555.

As shown in FIGS. 8A-9E, the reservoir assembly 114 may include a first fluid port, port 132 extending through an inner housing 130 of the reservoir assembly 114, the isolation structure 188 may be configured to expose the reservoir 119 to the nicotine vaporizer assembly 400 via the first fluid port 132 based on moving to the first position, and the isolation structure 188 may be further configured to cover the first fluid port 132 and thus isolate the nicotine vaporizer assembly 400 from the reservoir 119 based on moving to the second position. It will also be understood that, in some example embodiments, the inner housing 130 may be omitted from the reservoir assembly 114, such that the first fluid port 132 is also omitted.

As shown in at least FIGS. 2C-2D, the reservoir assembly 114 may include a second fluid port 150-i that is configured to enable fluid communication between the reservoir 119 and an exterior of the nicotine vapor generator assembly 110, the isolation structure 188 may be configured to cover the second fluid port 150-i to isolate the reservoir 119 from the exterior of the nicotine vapor generator assembly 110 based on moving to the first position, the isolation structure 188 may be further configured to expose the second port 150-i to expose the reservoir 119 to the exterior of the nicotine vapor generator assembly 110 based on moving to the second position, and the reservoir assembly 114 may be configured to be refilled through the second fluid port 150-i based on the isolation structure 188 being in the second position.

In some example embodiments, the isolation structure 188 may be configured to move in relation to both the reservoir assembly 114 and the reservoir assembly connector assembly 550 to a third position where the isolation structure covers both the first fluid port and the second fluid port, and the isolation structure 188 may be configured to open the connector conduit 555 to enable the connector element to disengage from the connector conduit 555 based on the isolation structure 188 moving to the third position.

In some example embodiments, the isolation structure 188 may include a third fluid port 188-o configured to at least partially align with the first fluid port 132 for the isolation structure 188 to expose the first fluid port 132 based on the isolation structure 188 moving to the first position.

It will also be understood that, in some example embodiments, the second fluid port 150-i, the coupling structure 160, the third fluid port 160-i, and/or the port adjustment ring 116 may be omitted from the reservoir assembly 114.

As shown in FIGS. 5A-5B, the reservoir assembly connector assembly 550 may be a bayonet connector that is configured to establish a bayonet interface connection with a bayonet connector, such as interlock structure 410, of the nicotine vaporizer assembly 400. But, in some example embodiments, the reservoir assembly connector assembly 550 may be configured to establish a different connection with the nicotine vaporizer assembly 400, including a threaded connection.

As shown in FIGS. 7A-9E, the isolation structure 188 may be configured to rotate around longitudinal axis 201 to move between the first position and the second position.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A nicotine vapor generator assembly comprising:
a reservoir assembly configured to hold a nicotine pre-vapor formulation in a reservoir; and
a nicotine vaporizer assembly configured to vaporize the nicotine pre-vapor formulation,
wherein the reservoir assembly further includes
a reservoir assembly connector assembly defining a connector conduit, the reservoir assembly connector assembly configured to detachably couple with the nicotine vaporizer assembly to establish fluid communication between the nicotine vaporizer assembly and the reservoir based on a connector element of the nicotine vaporizer assembly engaging with the connector conduit, and
an isolation structure configured to move in relation to both the reservoir and the reservoir assembly connector assembly between
a first position where the isolation structure exposes the nicotine vaporizer assembly to the reservoir and at least partially obstructs the connector conduit to restrict the connector element from disengaging from the connector conduit, and
a second position where the isolation structure isolates the nicotine vaporizer assembly from the reservoir and opens the connector conduit to enable the connector element to disengage from the connector conduit.

2. The nicotine vapor generator assembly of claim 1, wherein
the reservoir assembly includes a first fluid port extending through a housing of the reservoir assembly,
the isolation structure is configured to expose the reservoir to the nicotine vaporizer assembly via the first fluid port based on moving to the first position, and
the isolation structure is further configured to cover the first fluid port based on moving to the second position.

3. The nicotine vapor generator assembly of claim 2, wherein
the reservoir assembly includes a second fluid port, the second fluid port configured to enable fluid communication between the reservoir and an exterior of the nicotine vapor generator assembly,
the isolation structure is configured to cover the second fluid port to isolate the reservoir from the exterior of the nicotine vapor generator assembly based on moving to the first position,
the isolation structure is further configured to expose the second fluid port to expose the reservoir to the exterior of the nicotine vapor generator assembly based on moving to the second position, and the reservoir assembly is configured to be refilled through the second fluid port based on the isolation structure being in the second position.

4. The nicotine vapor generator assembly of claim 3, wherein
the isolation structure is further configured to move in relation to both the reservoir assembly and the reservoir assembly connector assembly to a third position where the isolation structure covers both the first fluid port and the second fluid port, and
the isolation structure is configured to open the connector conduit to enable the connector element to disengage from the connector conduit based on the isolation structure moving to the third position.

5. The nicotine vapor generator assembly of claim 2, wherein
the isolation structure includes a third fluid port configured to at least partially align with the first fluid port for the isolation structure to expose the first fluid port based on the isolation structure moving to the first position.

6. The nicotine vapor generator assembly of claim 1, wherein the reservoir assembly connector assembly is a bayonet connector that is configured to establish a bayonet interface connection with a bayonet connector of the nicotine vaporizer assembly.

7. The nicotine vapor generator assembly of claim 1, wherein the isolation structure is configured to rotate around a longitudinal axis of the reservoir assembly to move between the first position and the second position.

8. A nicotine e-vaping device, comprising:
the nicotine vapor generator assembly of claim 1; and
a power supply assembly coupled to the nicotine vapor generator assembly, the power supply assembly including a power supply, the power supply assembly configured to supply electrical power from the power supply to the nicotine vaporizer assembly.

9. The nicotine e-vaping device of claim 8, wherein the power supply is a rechargeable battery.

10. The nicotine e-vaping device of claim 8, wherein the power supply assembly is configured to decouple from the nicotine vapor generator assembly.

11. A reservoir assembly for a nicotine e-vaping device, the reservoir assembly comprising:
one or more structures defining a reservoir configured to hold a nicotine pre-vapor formulation;
a reservoir assembly connector assembly defining a connector conduit, the reservoir assembly connector assembly configured to detachably couple with a nicotine vaporizer assembly to establish fluid communication between the nicotine vaporizer assembly and the reservoir based on a connector element of the nicotine vaporizer assembly engaging with the connector conduit; and
an isolation structure configured to move in relation to both the reservoir and the reservoir assembly connector assembly between
a first position where the isolation structure exposes the nicotine vaporizer assembly to the reservoir and at least partially obstructs the connector conduit to restrict the connector element from disengaging from the connector conduit, and
a second position where the isolation structure isolates the nicotine vaporizer assembly from the reservoir and opens the connector conduit to enable the connector element to disengage from the connector conduit.

12. The reservoir assembly of claim 11, wherein
the reservoir assembly includes a first fluid port extending through a housing of the reservoir assembly,
the isolation structure is configured to expose the reservoir to the nicotine vaporizer assembly via the first fluid port based on moving to the first position, and
the isolation structure is further configured to cover the first fluid port based on moving to the second position.

13. The reservoir assembly of claim 12, wherein
the reservoir assembly includes a second fluid port, the second fluid port configured to enable fluid communication between the reservoir and an exterior of the reservoir assembly,
the isolation structure is configured to cover the second fluid port to isolate the reservoir from the exterior of the reservoir assembly based on moving to the first position,
the isolation structure is further configured to expose the second fluid port to expose the reservoir to the exterior of the reservoir assembly based on moving to the second position, and
the reservoir assembly is configured to be refilled through the second fluid port based on the isolation structure being in the second position.

14. The reservoir assembly of claim 13, wherein
the isolation structure is further configured to move in relation to both the reservoir assembly and the reservoir assembly connector assembly to a third position where the isolation structure covers both the first fluid port and the second fluid port, and
the isolation structure is configured to open the connector conduit to enable the connector element to disengage from the connector conduit based on the isolation structure moving to the third position.

15. The reservoir assembly of claim 14, wherein
the isolation structure includes a third fluid port configured to at least partially align with the first fluid port for the isolation structure to expose the first fluid port based on the isolation structure moving to the first position.

16. The reservoir assembly of claim 11, wherein the reservoir assembly connector assembly is a bayonet connector that is configured to establish a bayonet interface connection with a bayonet connector of the nicotine vaporizer assembly.

17. The reservoir assembly of claim 11, wherein the isolation structure is configured to rotate around a longitudinal axis of the reservoir assembly to move between the first position and the second position.

18. The reservoir assembly of claim 11, wherein the isolation structure is configured to move axially along a longitudinal axis of the isolation structure to move between the first position and the second position.

* * * * *